US007070929B2

(12) United States Patent
Tuggle et al.

(10) Patent No.: US 7,070,929 B2
(45) Date of Patent: Jul. 4, 2006

(54) GENETIC MARKERS FOR IMPROVED DISEASE RESISTANCE IN ANIMALS (BPI)

(75) Inventors: Christopher K. Tuggle, Ames, IA (US); Thomas J. Stabel, Ames, IA (US); Xianwei Shi, Kunming (CN); Martha A. Mellencamp, St. Joseph, MO (US)

(73) Assignees: Iowa State University Research Foundation, Inc., Ames, IA (US); Pig Inprovement Company UK Limited (GB); The United States of America as represented by the Secretary of Agriculture, Washington, DC (US)

( * ) Notice: Subject to any disclaimer, the term of this patent is extended or adjusted under 35 U.S.C. 154(b) by 396 days.

(21) Appl. No.: 10/161,968

(22) Filed: May 31, 2002

(65) Prior Publication Data

US 2003/0104424 A1    Jun. 5, 2003

Related U.S. Application Data

(60) Provisional application No. 60/294,668, filed on May 31, 2001.

(51) Int. Cl.
*C12Q 1/68* (2006.01)
*C12P 19/34* (2006.01)
*C07H 21/04* (2006.01)
*C07H 21/02* (2006.01)

(52) U.S. Cl. .................... 435/6; 435/91.1; 435/91.2; 536/23.5; 536/24.31

(58) Field of Classification Search .................... 435/6, 435/91.1, 91.2; 536/23.1, 23.7, 23.74, 24.3, 536/24.32, 24.33
See application file for complete search history.

(56) References Cited

FOREIGN PATENT DOCUMENTS

EP        02741782      2/2005

OTHER PUBLICATIONS

Huback et al. Clinical Chem Lab Medicine. 2002. 40(11): 1097-1100.*
Jagiello et al. International Journal of Immunogenetics. 2005. 32(1): 3-6.*
Leong, et al. Nucleotide sequence of the bovine bactericidal permeability increasing protein (BPI). Nucleic Acids Research. May 1990. vol. 18, No. 10, p. 3052.
Gray, et al. Cloning of the cDNA of a human neutrophil bactericidal protein: Structural and Functional correlations. Journal of Biological Chemistry. Jun. 5, 1989, vol. 264, No. 16, pp. 9505-9509.
Hubacek et al. Gene variants of the bactericidal/permeability Increasing protein and lipopolysaccharide binding protein in sepsis patients: Gender-specific genetic predisposition to sepsis. Critical Care Medicine. Mar. 2001, vol. 29, No. 3, pp. 557-561.
Hubacek et al. Short report on DNA marker at candidate locus. Clinical Genetics. Oct. 1997, vol. 52, No. 4, p. 249.
Gray, Patrick W., et al. "Cloning of the cDNA of a Human Neutrophil Bactericidal Protein" Journal of Biological Chemistry, vol. 264, No. 16, Jun. 5, 1980; pp. 9505-9509.
Gray, Patrick W., et al. "The Genes for the Lipopolysaccharide Binding Protein (LBP) and the Bactericidal Permeability Increasing Protein (BPI) are Encoded in the Same Region of Human Chromosome 20" Genomics 15, 188-190, 1993; XP-002318094.
Hollings, P.E., et al. "EcoRi and Bgill polymorphisms at the BPI-locus" Human Molecular Genetics, 1994, vol. 3, No. 2, 389.
Hubacek, Jaroslav A., et al. "Gene variants of the bactericidal/permeability increasing protein and lipopolysaccharide binding protein in sepsis patients; Gender-specific genetic predisposition to sepsis" Crit Care Med 2001, vol. 29, No. 3, pp. 557-561.
Hubacek, Jaroslav A., et al. "Short Report on DNA Marker at Candidate Locus" Genet 1997; 52:249, XP-002955925.
Jagiello, P., et al., Association Study of Wegener Granulomatosis and the Functionally Relevant A645G Polymorphism in the Bactericidal/Permeability Increasing Protein (BPI) Gene; 2005 Blackwell Publishing, International Journal of Immunogenetics 32, 3-6; XP-002318095.
Leong, Steven R., et al. Nucleotide Sequence of the Bovine Bactericidal Permeability Increasing Protein (BPI); 3052 Nucleic Acids Research, vol. 18, No. 10, 1990 Oxford University Press.
Vandermeer, Thomas J. et al., "Bactericidal/permeability-increasing Protein Amellorates Acute Lung Injury in Porcine Endotoxemia" 1994 American Physiological Society. pp. 2006-2014.

* cited by examiner

*Primary Examiner*—Carla J. Myers
(74) *Attorney, Agent, or Firm*—McKee, Voorhees & Sease, P.L.C.

(57) ABSTRACT

A method for determining improved disease resistance in animals is disclosed. The method assays for a novel genetic alleles of the BPI gene of the animal. The alleles are correlated with superior disease resistance. Novel nucleotide sequences, assays and primers are disclosed for the methods of the invention.

4 Claims, 7 Drawing Sheets

TGTGGAGGGCATCTCYGTTTGGCTAGTCTGCGGCTGGGTTATGACCCCACCTGCTGGGCTCCAGCTGCAGAAGCCACATCAACAGRGTCCACGT
ACGCACGTCCGGCAGCAGCCTGAAGTATGGTCTCCTGGGGCTGTGTTGGGAGGAGGGCTAGGRTTGTCTTAATCACTCTATTTTCCTTCTTACGGCCACACCTGCA
GGATATGGAAGTTCCTAGGCTAGGGGTTGAATCGGAGCTACACAGCTGCCCCCCTTACACCACAGCCAACACCAGATCCGAGCCTCATTTGCAACCTATGCCATAGCT
TGTTGGCAATGCCAGATCCTGAATCCACTGAGCGAGGATGGTACCCACATCCTCACAGATACTGGTCAGGTTCTTAACCCGCTGAGCCACAATGGGAATGCCACGT
CCTAATCATTCTTGTATTCAGAACACCCATCCTAAAAGCTGCCTCCATGCTAGGG

Figure 1

CTCAATCTGGGCCTCCTTCCCCCCGCACCTTACCGTGACCCCTCTGGCCTTGACCCTCACCTTTGTCCTGGAGACCCAGGCCTTTGCTGTCCTTCCGAACGCCTCCTTGGCC
CCCCTCTTCCKGATTGAGATGGTAAGCGGTTCCTGGGCGAGAGAGCCAGGTGGGAGCCTGGGAGCACTGCCTTCAGAGTCAGGGGACCATGCGACTCC
TACCCAGTCTCAAATCTGGCCTGTGGGTCTCCAGGGCCCGAGATGGGAGCCTCTGTCCTACTGCGTCTGGTTTTCTACAGTGTTCATTCATCCCATTATTCATTCTGTAGT
TGCCTTTGAAACCTGTGTGCTGTTTCCAGTGCATTCATTGTTTGGCCATTCATTGTGCATTTGCG

Figure 2

```
CTCATCTCTGGGCCTCCTTCCCCCCGCACCCTTACCGTGCACCCCTCTGGCCTTGACCTCACCCTTTGTCCTGAGACCCAGGCCCTTTGCTGTCCTTCCGAACGCCTCCTTGGCC
CCCCTCTTCCTGATTGAGATGGTAAGCGGTTCCTGGGCGAGAGAGCAGGTGGGAGCCCTGACACGGGGCTGGGAGCACTGCCTTCAGAGTCAGGGGACCCATGCGACTCC
TACCCAGTCTCAAATCTGGCCTGTGGGTCTCCAAGGCCCGAGATGGGAGCCCTCGTCCTGTCCTACTGCGTCTGGTTTCTACAGGTGTTCATTCATCCCATTATTCATTCTGTAGT
TGCCTTGAAACCTGTGTGCTGTTTCCAGTGCATTCATTCATTGCTCATTGTGCTCATTGCTCATTGATTCATTGATTTATTCAATTATTCATTC
AACTGCTAACTCGAAACATACCCTATCTCTTCCGGTTCACACATGCATTCGTTTATTCCATTATTCACTTATTACTTCCACCTCGTTCCACTGATGATTCATTTGT
ATATCTCTTTGTTCATTCATTCCTTTGACCAGTCTATCATCATCGTCTTCATCCATGCCTATCTTCATTCTTTATTCTTTCATTTGTGAGTTTAATCCTTATTGTTATTCCATTGTCGAT
TTGTGCATTCATTCCTTTGACCAGTCTATCACTCCATGAACATTTGGTGGCTGGCATCCATTCCACTTTGGCCACTGGAGGTGAAGGCCAGACCCTCCTCACCAGGAGGTACTCAA
AGGGCTGCCCCGTCTCAAGTTGGAGACCCATTTCCCCACACCAGTCAGTGCATACATGAATGTGTTGAGAACAGGGTTGGCTAGGATTCCAGCTCTACCGTATGATGCTTGTAACCCACGGAGTGG
TCTAAACTCAGTCAGCGTTTGTTGAGTGCATACATGAATGTGTTGAGAACAGGGTTGGCTAGGATTCCAGCTCTACCGTATGATGCTTGTAACCCACGGAGTGG
CCTGAGGACTCTAAAATGGTCTCAGAAGCACCGGAGAAGCTAATGGTTGACCATCCAGCACTCAGCAAGGGCCCAAAGCAAAAGGATGTGCATCTGTGGGTTTG
TAAGTCTGACCTGGCGGTGGTTGGGGGCTCTTCTGCTTGAGCCTTGAGAAGCTGACCTTCCTCGTCTTGGTCTTGGAGGCTTCACGAGTCGCTGGTCCTGGGTCAGGGGACTTCA
CTTCCTGGCTTGTGTTGCTTTGCAGAACAGCAGCATTTCTGTGACATG
```

Figure 3

```
                                   24                                                           54
3 allele:   1  atggccaggggcgctgacaacacactcaggtgggcgactctgttggcgctggctgccctg         60
4 allele:   1  atggccaggggcgctgacaacacagctcaggtgggcgactctgttggcgctggcgccctg         60

3 allele:  61  ggcacagctgtgacagcggctgccaacccgcattgtggccaggatcacacagaagggc      120
4 allele:  61  ggcacagctgtgacagcggctgccaacccgcattgtggccaggatcacacagaagggc      120

3 allele: 121  ctggactacgcctgccagcaggagtggctactctgcggaaggagctggagaagatcacg    180
4 allele: 121  ctggactacgcctgccagcaggagtggctactctgcggaaggagctggagaagatcacg    180

3 allele: 181  attcccactttctccggaagctttaagatcaagtactttgggaaaggacgttataacttc   240
4 allele: 181  attcccactttctccggaagctttaagatcaagtactttgggaaaggacgttataacttc   240

3 allele: 241  tacagcatggttgttcgtgaattcaagcttcccacttcccagataagactgtcacctgac   300
4 allele: 241  tacagcatggttgttcgtgaattcaagcttcccacttcccagataagactgtcacctgac   300

3 allele: 301  cagggccttgatctctccatcaaagatgccagtgccagtgtcaagatcagtggaaaatggaaggcc   360
4 allele: 301  cagggccttgatctctccatcaaagatgccagtgccagtgtcaagatcagtggaaaatggaaggcc   360
                                                                          384
3 allele: 361  caaaagaatttcatcaaagccagtggcaacctttgacctgagtgtggagggcatctccgtt      420
4 allele: 361  caaaagaatttcatcaaagccagcggcaacctttgacctgagtgtggagggcatctccgtt      420
                                                        456
3 allele: 421  ttggctagtctgcgctgggtttatgaccccacctctgccactccaccgtcctcctgctcc    480
4 allele: 421  ttggctagtctgcgctgggtttatgaccccacctctgccactccaccgtcctcctgctcc    480
                                                       504
3 allele: 481  agctgcagaagccacatcaacaggtccacgtacgcacgtccggcacgtccggcagcgaagtgg      540
4 allele: 481  agctgcagaagccacatcaacagagtccacgtacgcacgtccggcacgtccggcagcgaagtgg   540
```

*Figure 4A*

```
3 allele: 541  ctgatccagctcttccacagaaatatcgcgctccgaaaagccatggagagcaag  600
4 allele: 541  ctgatccagctcttccacagaaatatcgcgctccgaaaagccatggagagcaag  600

3 allele: 601  atctgtaagatgttgaccaataccgtgtcctccaagctgcagcccttattccagaccctg  660
4 allele: 601  atctgtaagatgttgaccaataccgtgtcctccaagctgcagcccttattccagaccctg  660

3 allele: 661  ccagtgacagccaaagtggacagaatggttggcatcaattactccctggtggcacctcca  720
4 allele: 661  ccagtgacagccaaagtggacagaatggttggcatcaattactccctggtggcacctcca  720

3 allele: 721  aaagccacggctgagaacctggatgggctgctgaaggggagttttttcagcctggaccac  780
4 allele: 721  aaagccacggctgagaacctggatgggctgctgaagggggagttttttcagcctggaccac  780
                                                       807
3 allele: 781  cctagccccctccctttgccccgccgcactggcccttcctgccgaccaccgaccgcatg  840
4 allele: 781  cctagccccctccctttgccccgcctgcactggcccttcctgccgaccaccgaccgcatg  840
                                                       879
3 allele: 841  gtgtatctgtgcatctccgaatacttcttcaacacggccgggctggtgtaccaaaaggct  900
4 allele: 841  gtgtatctgtgcatctccgaatacttcttcaacacggctgggctggtgtaccaaaaggct  900

3 allele: 901  ggagtcctgaatctgaccatcaacaacagcatgattccaaagaaatctctgttcagcctg  960
4 allele: 901  ggagtcctgaatctgaccatcaacaacagcatgattccaaagaaatctctgttcagcctg  960

3 allele: 961  acaaccaacttcttggaactctcataccaaggtgtccacgatgttcccaacatggag  1020
4 allele: 961  acaaccaacttcttggaactctcataccaaggtgtccacgatgttcccaacatggag  1020
                                                       1060
3 allele: 1021 atgcagttcctcatctgggcctccttcccccgccaccttgccgtgcaccctctggcctt  1080
4 allele: 1021 atgcagttcctcatctgggcctccttcccccgccaccttaccgtgcaccctctggccttt  1080
```

*Figure 4B*

```
3 allele: 1081 gacctcacctttgtcctgagaccaggcctttgctgtcttccgaacgcctccttggcc 1140
4 allele: 1081 gacctcacctttgtcctgagaccaggcctttgctgtcttccgaacgcctccttggcc 1140
                                    1051
3 allele: 1141 cccctcttccggattgagatgaacagcagcatttctgtggacattggtgtccggtccaaa 1200
4 allele: 1141 cccctcttcctgattgagatgaacagcagcatttctgtggacattggtgtccggtccaaa 1200
3 allele: 1201 aggcttattggagagctcaggttgaacaagctgctcctggaactgaagcactcaaacatc 1260
4 allele: 1201 aggcttattggagagctcaggttgaacaagctgctcctggaactgaagcactcaaacatc 1260
3 allele: 1261 ggcccctctctcggtggaattgctgcaggctgtcatgaactttgccgtgccactcttgtg 1320
4 allele: 1261 ggcccctctctcggtggaattgctgcaggctgtcatgaactttgccgtgccactcttgtg 1320
3 allele: 1321 cttcccaagattaatgagaagctgcagagaggcttcctctccgtgccgcctacatc 1380
4 allele: 1321 cttcccaagattaatgagaagctgcagagaggcttcctctccgtgccgcctacatc 1380
3 allele: 1381 cagctctccaacctggtgcttcagcctcatcaggattcctgctgtttggtgcagatgtc 1440
4 allele: 1381 cagctctccaacctggtgcttcagcctcatcaggattcctgctgtttggtgcagatgtc 1440
3 allele: 1441 cgctatagctga 1452
4 allele: 1441 cgctatagctga 1452
```

*Figure 4C*

```
1 porcine a3  100.0%  ----MARGADNTLRWATLVALAALGTAVTAAANPGIVARITQKGLDYACQQGVATLRKEL  56
2 porcine a4   99.6%  ----MARGADNTLRWATLVALAALGTAVTAAANPGIVARITQKGLDYACQQGVATLRKEL  56
3 human BPI    63.4%  MRENMARGPCNAPRWVSLMVLVAIGTAVTAAVNPGVVVRISQKGLDYASQQGTAALQKEL  60
4 human LBP    43.1%  ------MGALARALPSILLALLLTSTPEALGANPGLVARITDKGLQYAAQEGLLALQSEL  54
5 human PLTP   27.1%  -------------MVLLWALFLALLAG----AHAELPGCKIRVTSAALDLVKQEGLRFLEQEL  46
6 human CETP   17.0%  --------MLAATVLTLALLGNAHACSKGTSHEAGIVCRITKPALLVLNHETAKVIQTAF  52

1 porcine a3  100.0%  EKITIPTFSGSFKIKYFGKGRYNFYSMVREFKLPTSQIRLSPDQGLDLSIKDASVKISG  116
2 porcine a4   99.6%  EKITIPTFSGSFKIKYFGKGRYNFYSMVREFKLPTSQIRLSPDQGLDLSIKDASVKISG  116
3 human BPI    63.4%  KRIKIPDYSDSFKIKHLGKGHYSFYSMDIREFQLPSSQISMVPNVGLKFSISNANIKISG  120
4 human LBP    43.1%  LRITLPDFTGDLRIPHVGRGRYEFHSLNIHSCELLHSALRPVPGQGLSLSISDSSIRVQG  114
5 human PLTP   27.1%  ETITIPDVYG------AKGHFYYNISDVRVTQLHLISSELHFQPDQDLLLNISNASLGLHF  101
6 human CETP   17.0%  QRASYPDITGEKAMMLLGQVKYGLHNIQISHLSIASSQVELVEAKSIDVSIQNVSVVFKG  112

1 porcine a3  100.0%  KWKA---QKNFIKASGNFDLSVEGISVLASLRLGYDPTSGHSTVSCSSCRSHINRVHVRT  173
2 porcine a4   99.6%  KWKA---QKNFIKASGNFDLSVEGISVLASLRLGYDPTSGHSTVSCSSCRSHINRVHVRT  173
3 human BPI    63.4%  KWKA---QKRFLKMSGNFDLSIEGMSISADLKLGSNPTSGKPTITCSSCSSHINSVHVHI  177
4 human LBP    43.1%  RWKV---RKSFFKLQGSFDVSVKGISISVNLLLGSE-SSGRPTGYCLSCSSDIADVEVDM  171
5 human PLTP   27.1%  RRQL---LYWFLYDGGYINASAEGVSIRTGLQLSQD-SSGRIKVSNVSCEASVSKMNMAF  158
6 human CETP   17.0%  TLKYGYTTAWMLGIDQSIDFEID-SAIDLQINTQLTCDSGRVRTDAPDCYLSFHKLLLHL  171

1 porcine a3  100.0%  SGSSL-KWLIQLFHRNIESALRKAMESKICKMLTNTVSSKLQPYFQTLPVTAKVDRMVGI  232
2 porcine a4   99.6%  SGSSL-KWLIQLFHRNIESALRKAMESKICKMLTNTVSSKLQPYFQTLPVTAKVDRMVGI  232
3 human BPI    63.4%  SKSKV-GWLIQLFHKKIESALRNKMNSQVCEKVTNSVSSKLQPYFQTLPVMTKIDSVAGI  236
4 human LBP    43.1%  SGDS--GWLLNLFHNQIESKFQKVLESRICEMIQKSVSSDLQPYLQTLPVTTEIDSFADI  229
5 human PLTP   27.1%  -GGTF-RRMYNFFSTFITSGMRFLLNQQICPVLYHAGTVLLNSLLDTVPVRSSVDDLVGI  216
6 human CETP   17.0%  QGEREPGWIKQLFTNFISFTLKLVLKGQICKEIN-VISNIMADFVQTRAASILSDGDIGV  230
```

*Figure 5A*

| | | | |
|---|---|---|---|
| 1 porcine a3 | 100.0% | NYSLVAPPKATAENLDGLLKGEFFSLDHPSPPFAPPALALPADHDRMVYLCISEYFFNT | 292 |
| 2 porcine a4 | 99.6% | NYSLVAPPKATAENLDGLLKGEFFSLDHPSPPFAPPALALPADHDRMVYLCISEYFFNT | 292 |
| 3 human BPI | 63.4% | NYGLVAPPATTAETLDVQMKGEFYSENHHNPPPFAPPVMEFPAAHDRMVYLGLSDYFFNT | 296 |
| 4 human LBP | 43.1% | DYSLVEAPRATAQMLEVMFKGEIFHRNHRSP----VTLLAAAEEHNKMVYFAISDYVFNT | 285 |
| 5 human PLTP | 27.1% | DYSLLKDPVVSNGNLDMEFRGAFFPLKEDNWSLPNRAVEPQLEDDERMVYAFSEFFFDS | 276 |
| 6 human CETP | 17.0% | DISLTGDPVITASYLESHHKGHFTYKN-VSEDLPLPTFSPTLLGDSRMLYFWFSERVFHS | 289 |
| | | | |
| 1 porcine a3 | 100.0% | AGLVYQKAGVLNLTINNSMIPKKSLFSLTTNFFGTLIPKVSTMFPNMEMQFLIWASFPPH | 352 |
| 2 porcine a4 | 99.6% | AGLVYQKAGVLNLTINNSMIPKKSLFSLTTNFFGTLIPKVSTMFPNMEMQFLIWASFPPH | 352 |
| 3 human BPI | 63.4% | AGLVYQEAGVLKMTLRDDMIPKESKFRLTTKFFGTFLPEVAKKFPNMKIQIHVSASTPPH | 356 |
| 4 human LBP | 43.1% | ASLVYHEEGYLNFSITDDMIPPDSNIRLTTKSFRPFVPRLARLYPNMNLELQGSVPSAPL | 345 |
| 5 human PLTP | 27.1% | AMESYFQAGALQLTLVGDKVPSDLDMLLRATYFGSIVLLSPTVIN-SPLKLKLEATSPPR | 335 |
| 6 human CETP | 17.0% | LAKVAFQDGRLMLSLMG----DEFKAVLETWGFNTNQEIFQEVVGGFPSQAQVTVHCLKM | 345 |
| | | | |
| 1 porcine a3 | 100.0% | LAVHPSGLDLTFVLETQAFAVLPNASLAPLFRIEMNSSISVDIGVRSKRLIGELRLNKLL | 412 |
| 2 porcine a4 | 99.6% | LTVHPSGLDLTFVLETQAFAVLPNASLAPLFLIEMNSSISVDIGVRSKRLIGELRLNKLL | 412 |
| 3 human BPI | 63.4% | LSVQPTGLTFYPAVDVQAFAVLPNSSLASLFLGMHTTGSMEVSAESNRLVGELKLDRLL | 416 |
| 4 human LBP | 43.1% | LNFSPGNLSVDPYMEIDAFVLLPSSKEPVFRLSVATNVSATLTFNTSKITGFLKPGKVK | 405 |
| 5 human PLTP | 27.1% | CTIKPSGTTISITASVTITLAPPMLPEVELSKMIMEGRLSAKLTLRGKALRVKLDLRRFQ | 395 |
| 6 human CETP | 17.0% | PKISCQNKGVVVNSSVMVKFLFPRPDQQHSVAYTFEEDIVTVQASYSKKKLFLSLLDFQ | 405 |
| | | | |
| 1 porcine a3 | 100.0% | LELK-HSNIGPFSVELLQAVMNFAVPTLVLPKINEKLQRGFPLPLPAY----IQLSNLVL | 467 |
| 2 porcine a4 | 99.6% | LELK-HSNIGPFSVELLQAVMNFAVPTLVLPKINEKLQRGFPLPLPAY----IQLSNLVL | 467 |
| 3 human BPI | 63.4% | LELK-HSNIGPFPVELLQDIMNYIVPILVLPRVNEKLQKGFPLPTPAR----VQLYNVVL | 471 |
| 4 human LBP | 43.1% | VELK-ESKVGLFNAELLEALLNYILNTLYPKFNDKLAEGFPLPLLKR----VQLYDLGL | 460 |
| 5 human PLTP | 27.1% | IYSN-QSALESLALIPLQAPLKTLLQIGVMPLLNERTWRGVQIPLPEG----INFVREVV | 450 |
| 6 human CETP | 17.0% | ITPKTVSNLTESSSESIQSFLQSMITAVGIPEVMSRLEVVFTALMNSKGVSLFDIINPEI | 465 |
| | | | |
| 1 porcine a3 | 100.0% | QPHQDFLLFGADVRYS------------- | 483 |
| 2 porcine a4 | 99.6% | QPHQDFLLFGADVRYS------------- | 483 |
| 3 human BPI | 63.4% | QPHQNFLLFGADVVYK------------- | 487 |
| 4 human LBP | 43.1% | QIHKDFLFLGANVQYMRV----------- | 478 |
| 5 human PLTP | 27.1% | TNHAGFVTVGADLHFAKGLREVIDKNRPADVAASHVPPSAAAA | 494 |
| 6 human CETP | 17.0% | ITRDGFLLLQMDFGFPEHLLVDFLQSLS-- | 493 |

*Figure 5B*

SEQUENCE LISTING

<160> NUMBER OF SEQ ID NOS: 16

<210> SEQ ID NO 1
<211> LENGTH: 20

```
<212> TYPE: DNA
<213> ORGANISM: Sus scrofa

<400> SEQUENCE: 1
ggtggcaact ttgacctgag                                                    20

<210> SEQ ID NO 2
<211> LENGTH: 21
<212> TYPE: DNA
<213> ORGANISM: Sus scrofa

<400> SEQUENCE: 2
catcggaggt ctctggacaa g                                                  21

<210> SEQ ID NO 3
<211> LENGTH: 499
<212> TYPE: DNA
<213> ORGANISM: Sus scrofa

<400> SEQUENCE: 3
tgtggagggc atctcygttt tggctagtct gcggctgggt tatgacccca cctcgggcca        60
ctccaccgtc tcctgctcca gctgcagaag ccacatcaac agrgtccacg tacgcacgtc       120
cggcagcagc ctgaagtatg gtctcctggg gctgtggttg ggaggagggc taggrttgtc       180
ttaatcactc tattttcct tcttcttacg gccacacctg caggatatgg aagttcctag        240
gctaggggtt gaatcggagc tacagctgcc cccttacac cacagccaca gcaacaccag        300
atccgagcct catttgcaac ctatgccata gcttgtggca atgccagatc ctgaatccac       360
tgagcgaggc cagggatggt acccacatcc tcacagatac tggtcaggtt cttaacccgc       420
tgagccacaa tgggaatgcc acgtcctaat cattcttgta ttcagaacac ccatcctaaa       480
agctgcctcc atgctaggg                                                   499

<210> SEQ ID NO 4
<211> LENGTH: 18
<212> TYPE: DNA
<213> ORGANISM: Sus scrofa

<400> SEQUENCE: 4
cccaacatgg agatgcag                                                      18

<210> SEQ ID NO 5
<211> LENGTH: 21
<212> TYPE: DNA
<213> ORGANISM: Sus scrofa

<400> SEQUENCE: 5
caatgaatca atgagcacac c                                                  21

<210> SEQ ID NO 6
<211> LENGTH: 406
<212> TYPE: DNA
<213> ORGANISM: Sus scrofa

<400> SEQUENCE: 6
ttcctcatct gggcctcctt cccccgcac cttaccgtgc acccctctgg ccttgacctc         60 accttttgtcc tggagaccca ggcctttgct gtccttccga acgcctcctt ggcccccctc     120
ttcckgattg agatggtaag cggttcctgg gcgagagagc aggtgggag ccctggacgg        180 gggctgggag cactgccttc agagtcaggg gacccatgcg actcctaccc agtctcaaat       240
```

| | |
|---|---|
| ctggcctgtg ggtctccagg gcccgagatg ggagcctctg tcctactgcg tctggtttct | 300 |
| acaggtgttc attcatccca ttattcattc tgtagttgcc ttgaaacctg tgtgctgttt | 360 |
| ccagtgcatt cattcatatc tttggccatt ccattgtgca tttgcg | 406 |

<210> SEQ ID NO 7
<211> LENGTH: 20
<212> TYPE: DNA
<213> ORGANISM: Sus scrofa

<400> SEQUENCE: 7

| | |
|---|---|
| aagccttttg gaccggacac | 20 |

<210> SEQ ID NO 8
<211> LENGTH: 1268
<212> TYPE: DNA
<213> ORGANISM: Sus scrofa

<400> SEQUENCE: 8

| | |
|---|---|
| ctcatctggg cctccttccc cccgcacctt accgtgcacc cctctggcct tgacctcacc | 60 |
| tttgtcctgg agacccaggc ctttgctgtc cttccgaacg cctccttggc cccctcttc | 120 |
| ctgattgaga tggtaagcgg ttcctgggcg agagagcagg tggggagccc tggacggggg | 180 |
| ctgggagcac tgccttcaga gtcaggggac ccatgcgact cctacccagt ctcaaatctg | 240 |
| gcctgtgggt ctccagggcc cgagatggga gcctctgtcc tactgcgtct ggtttctaca | 300 |
| ggtgttcatt catcccatta ttcattctgt agttgcttg aaacctgtgt gctgtttcca | 360 |
| gtgcattcat tcatatcttt ggccattcca ttgtgcattt gcggtgtgc tcattgattc | 420 |
| attgatttat tcaattattc attcaactgc taactcgaaa catacccctat ctcttccggt | 480 |
| tcacacatgc attcgtttat tccattattc acttattcat ttacttccac ctcgttccac | 540 |
| tgatgattca tttgtatatc tctttgttca ttcattcatc atgtcttcat ccatgcctat | 600 |
| ctttatttat tctttcattt gtgagtttaa tccttcactt attcaaatgt ttattccatt | 660 |
| gtcgatttgt gcattcattc ctttgaccag tctatcactc catgaacatt tggtggctgg | 720 |
| catccacttt ggccactgga ggtgaaggcc agaccctcct caccaggagg tactcaaagg | 780 |
| gctgccccgt ctcaagttga gacccatttt ccccacaccg cagatgcagt ggattctgag | 840 |
| aggctccccc aagtcacac aggaaagcgg aaggggggaac cttggttttc taaactcagt | 900 |
| cagcgtttgt tgagtgcata catgaatgaa tgtgtgttga gaacaggggtt ggctaggatt | 960 |
| ccagctctac cgtatgatgc ttgtaaccca cgggagtggc ctgaggactc taaaatggtc | 1020 |
| tcagaagcac cgggagacaa tggtaattgg ttgaccatcc agcactcagc aaggggccca | 1080 |
| aagcaaaagg atgtgcatct gtgggttttg taagtctgac ctggcggtgg ttgggggggct | 1140 |
| cttctgctga gcctttgaga agctgacctt ctggtcttgg aggcttcaca gagtcgctgg | 1200 |
| tgcctgggtc aggggacttc acttcctggc ttgttgcttt gcagaacagc agcatttctg | 1260 |
| tggacatg | 1268 |

<210> SEQ ID NO 9
<211> LENGTH: 1392
<212> TYPE: DNA
<213> ORGANISM: Sus Scrofa

<400> SEQUENCE: 9

| | |
|---|---|
| ctggactacg cctgccagca gggagtggct actctgcgga aggagctgga gaagatcacg | 60 |
| attcccactt tctccggaag ctttaagatc aagtactttg ggaaggacg ttataacttc | 120 |

```
attcccactt tctccggaag ctttaagatc aagtactttg ggaaaggacg ttataacttc      180
tacagcatgg ttgttcgtga attcaagctt cccacttccc agataagact gtcacctgac      240
cagggccttg atctctccat caaagatgcc agtgtcaaga tcagtggaaa atggaaggcc      300
caaaagaatt tcatcaaagc cagtggcaac tttgacctga gtgtggaggg catctccgtt      360
ttggctagtc tgcggctggg ttatgacccc acctctggcc actccaccgt ctcctgctcc      420
agctgcagaa gccacatcaa cagggtccac gtacgcacgt ccggcagcag cctgaagtgg      480
ctgatccagc tcttccacag aaatatcgaa tctgcgctcc gaaaagccat ggagagcaag      540
atctgtaaga tgttgaccaa taccgtgtcc tccaagctgc agccttattt ccagaccctg      600
ccagtgacag ccaaagtgga cagaatggtt ggcatcaatt actccctggt ggcacctcca      660
aaagccacgg ctgagaacct ggatgggctg ctgaaggggg agttttttcag cctggaccac      720 cctagccccc ctccctttgc cccgccggca ctggcccttc ctgccgacca cgaccgcatg      780
gtgtatctgt gcatctccga atacttcttc aacacggccg ggctggtgta ccaaaaggct      840
ggagtcctga atctgaccat caacaacagc atgattccaa agaaatctct gttcagcctg      900
acaaccaact tctttggaac tctcataccc aaggtgtcca cgatgttccc caacatggag      960
atgcagttcc tcatctgggc ctccttcccc ccgcaccttg ccgtgcaccc ctctggcctt     1020
gacctcacct ttgtcctgga gacccaggcc tttgctgtcc ttccgaacgc ctccttggcc     1080
cccctcttcc ggattgagat gaacagcagc atttctgtgg acattggtgt ccggtccaaa     1140
aggcttattg gagagctcag gttgaacaag ctgctcctgg aactgaagca ctcaaacatc     1200
ggccccttct cggtggaatt gctgcaggct gtcatgaact ttgccgtgcc cactcttgtg     1260
cttcccaaga ttaatgagaa gctgcagaga ggctttcctc tcccgctgcc cgcctacatc     1320
cagctctcca acctggtgct tcagcctcat caggatttcc tgctgtttgg tgcagatgtc     1380
cgctatagct ga                                                         1392

<210> SEQ ID NO 10
<211> LENGTH: 1452
<212> TYPE: DNA
<213> ORGANISM: Sus scrofa

<400> SEQUENCE: 10
atggccaggg gcgctgacaa cacgctcagg tgggcgactc tggtggcgct ggccgccctg       60
ggcacagctg tgacagcggc tgccaacccc ggcattgtgg ccaggatcac acagaagggc      120
ctggactacg cctgccagca gggagtggct actctgcgga aggagctgga agatcacg       180 attcccactt tctccggaag ctttaagatc aagtactttg ggaaaggacg ttataacttc      240
tacagcatgg ttgttcgtga attcaagctt cccacttccc agataagact gtcacctgac      300
cagggccttg atctctccat caaagatgcc agtgtcaaga tcagtggaaa atggaaggcc      360
caaaagaatt tcatcaaagc cagcggcaac tttgacctga gtgtggaggg catctccgtt      420
ttggctagtc tgcggctggg ttatgacccc acctcgggcc actccaccgt ctcctgctcc      480
agctgcagaa gccacatcaa cagagtccac gtacgcacgt ccggcagcag cctgaagtgg      540
ctgatccagc tcttccacag aaatatcgaa tctgcgctcc gaaaagccat ggagagcaag      600
atctgtaaga tgttgaccaa taccgtgtcc tccaagctgc agccttattt ccagaccctg      660
ccagtgacag ccaaagtgga cagaatggtt ggcatcaatt actccctggt ggcacctcca      720
aaagccacgg ctgagaacct ggatgggctg ctgaaggggg agttttttcag cctggaccac      780
```

```
cctagccccc ctcccttttgc cccgcctgca ctggcccttc ctgccgacca cgaccgcatg   840
gtgtatctgt gcatctccga atacttcttc aacacggctg ggctggtgta ccaaaaggct   900
ggagtcctga atctgaccat caacaacagc atgattccaa agaaatctct gttcagcctg   960
acaaccaact tctttggaac tctcataccc aaggtgtcca cgatgttccc caacatggag  1020
atgcagttcc tcatctgggc ctccttcccc ccgcaccta ccgtgcaccc ctctggcctt  1080
gacctcacct ttgtcctgga gacccaggcc tttgctgtcc ttccgaacgc ctccttggcc  1140
cccctcttcc tgattgagat gaacagcagc atttctgtgg acattggtgt ccggtccaaa  1200
aggcttattg gagagctcag gttgaacaag ctgctcctgg aactgaagca ctcaaacatc  1260
ggccccttct cggtggaatt gctgcaggct gtcatgaact ttgccgtgcc cactcttgtg  1320
cttcccaaga ttaatgagaa gctgcagaga ggctttcctc tcccgctgcc cgcctacatc  1380
cagctctcca acctggtgct tcagcctcat caggatttcc tgctgtttgg tgcagatgtc  1440
cgctatagct ga                                                      1452
```

<210> SEQ ID NO 11
<211> LENGTH: 367
<212> TYPE: PRT
<213> ORGANISM: Sus scrofa

<400> SEQUENCE: 11

```
Lys Trp Lys Ala Gln Lys Asn Phe Ile Lys Ala Ser Gly Asn Phe Asp
1               5                   10                  15

Leu Ser Val Glu Gly Ile Ser Val Leu Ala Ser Leu Arg Leu Gly Tyr
            20                  25                  30

Asp Pro Thr Ser Gly His Ser Thr Val Ser Cys Ser Ser Cys Arg Ser
        35                  40                  45

His Ile Asn Arg Val His Val Arg Thr Ser Gly Ser Ser Leu Lys Trp
    50                  55                  60

Leu Ile Gln Leu Phe His Arg Asn Ile Glu Ser Ala Leu Arg Lys Ala
65                  70                  75                  80

Met Glu Ser Lys Ile Cys Lys Met Leu Thr Asn Thr Val Ser Ser Lys
                85                  90                  95

Leu Gln Pro Tyr Phe Gln Thr Leu Pro Val Thr Ala Lys Val Asp Arg
            100                 105                 110

Met Val Gly Ile Asn Tyr Ser Leu Val Ala Pro Pro Lys Ala Thr Ala
        115                 120                 125

Glu Asn Leu Asp Gly Leu Leu Lys Gly Glu Phe Phe Ser Leu Asp His
    130                 135                 140

Pro Ser Pro Pro Phe Ala Pro Pro Leu Ala Leu Pro Ala Asp
145                 150                 155                 160

His Asp Arg Met Val Tyr Leu Cys Ile Ser Glu Tyr Phe Asn Thr
                165                 170                 175

Ala Gly Leu Val Tyr Gln Lys Ala Gly Val Leu Asn Leu Thr Ile Asn
            180                 185                 190

Asn Ser Met Ile Pro Lys Lys Ser Leu Phe Ser Leu Thr Thr Asn Phe
        195                 200                 205

Phe Gly Thr Leu Ile Pro Lys Val Ser Thr Met Phe Pro Asn Met Glu
    210                 215                 220

Met Gln Phe Leu Ile Trp Ala Ser Phe Pro Pro His Leu Ala Val His
225                 230                 235                 240

Pro Ser Gly Leu Asp Leu Thr Phe Val Leu Glu Thr Gln Ala Phe Ala
                245                 250                 255
```

```
Val Leu Pro Asn Ala Ser Leu Ala Pro Leu Phe Arg Ile Glu Met Asn
            260                 265                 270

Ser Ser Ile Ser Val Asp Ile Gly Val Arg Ser Lys Arg Leu Ile Gly
            275                 280                 285

Glu Leu Arg Leu Asn Lys Leu Leu Glu Leu Lys His Ser Asn Ile
        290                 295                 300

Gly Pro Phe Ser Val Glu Leu Leu Gln Ala Val Met Asn Phe Ala Val
305                 310                 315                 320

Pro Thr Leu Val Leu Pro Lys Ile Asn Glu Lys Leu Gln Arg Gly Phe
                325                 330                 335

Pro Leu Pro Leu Pro Ala Tyr Ile Gln Leu Ser Asn Leu Val Leu Gln
            340                 345                 350

Pro His Gln Asp Phe Leu Leu Phe Gly Ala Asp Val Arg Tyr Ser
        355                 360                 365

<210> SEQ ID NO 12
<211> LENGTH: 483
<212> TYPE: PRT
<213> ORGANISM: Sus scrofa

<400> SEQUENCE: 12

Met Ala Arg Gly Ala Asp Asn Thr Leu Arg Trp Ala Thr Leu Val Ala
1               5                   10                  15

Leu Ala Ala Leu Gly Thr Ala Val Thr Ala Ala Asn Pro Gly Ile
            20                  25                  30

Val Ala Arg Ile Thr Gln Lys Gly Leu Asp Tyr Ala Cys Gln Gln Gly
            35                  40                  45

Val Ala Thr Leu Arg Lys Glu Leu Glu Lys Ile Thr Ile Pro Thr Phe
        50                  55                  60

Ser Gly Ser Phe Lys Ile Lys Tyr Phe Gly Lys Gly Arg Tyr Asn Phe
65                  70                  75                  80

Tyr Ser Met Val Val Arg Glu Phe Lys Leu Pro Thr Ser Gln Ile Arg
                85                  90                  95

Leu Ser Pro Asp Gln Gly Leu Asp Leu Ser Ile Lys Asp Ala Ser Val
            100                 105                 110

Lys Ile Ser Gly Lys Trp Lys Ala Gln Lys Asn Phe Ile Lys Ala Ser
        115                 120                 125

Gly Asn Phe Asp Leu Ser Val Glu Gly Ile Ser Val Leu Ala Ser Leu
130                 135                 140

Arg Leu Gly Tyr Asp Pro Thr Ser Gly His Ser Thr Val Ser Cys Ser
145                 150                 155                 160

Ser Cys Arg Ser His Ile Asn Arg Val His Val Arg Thr Ser Gly Ser
                165                 170                 175

Ser Leu Lys Trp Leu Ile Gln Leu Phe His Arg Asn Ile Glu Ser Ala
            180                 185                 190

Leu Arg Lys Ala Met Glu Ser Lys Ile Cys Lys Met Leu Thr Asn Thr
        195                 200                 205

Val Ser Ser Lys Leu Gln Pro Tyr Phe Gln Thr Leu Pro Val Thr Ala
    210                 215                 220

Lys Val Asp Arg Met Val Gly Ile Asn Tyr Ser Leu Val Ala Pro Pro
225                 230                 235                 240

Lys Ala Thr Ala Glu Asn Leu Asp Gly Leu Leu Lys Gly Glu Phe Phe
                245                 250                 255

Ser Leu Asp His Pro Ser Pro Pro Phe Ala Pro Pro Ala Leu Ala
```

-continued

```
            260                 265                 270
Leu Pro Ala Asp His Asp Arg Met Val Tyr Leu Cys Ile Ser Glu Tyr
        275                 280                 285
Phe Phe Asn Thr Ala Gly Leu Val Tyr Gln Lys Ala Gly Val Leu Asn
    290                 295                 300
Leu Thr Ile Asn Asn Ser Met Ile Pro Lys Lys Ser Leu Phe Ser Leu
305                 310                 315                 320
Thr Thr Asn Phe Phe Gly Thr Leu Ile Pro Lys Val Ser Thr Met Phe
                325                 330                 335
Pro Asn Met Glu Met Gln Phe Leu Ile Trp Ala Ser Phe Pro Pro His
            340                 345                 350
Leu Thr Val His Pro Ser Gly Leu Asp Leu Thr Phe Val Leu Glu Thr
        355                 360                 365
Gln Ala Phe Ala Val Leu Pro Asn Ala Ser Leu Ala Pro Leu Phe Leu
    370                 375                 380
Ile Glu Met Asn Ser Ser Ile Ser Val Asp Ile Gly Val Arg Ser Lys
385                 390                 395                 400
Arg Leu Ile Gly Glu Leu Arg Leu Asn Lys Leu Leu Leu Glu Leu Lys
                405                 410                 415
His Ser Asn Ile Gly Pro Phe Ser Val Glu Leu Leu Gln Ala Val Met
            420                 425                 430
Asn Phe Ala Val Pro Thr Leu Val Leu Pro Lys Ile Asn Glu Lys Leu
        435                 440                 445
Gln Arg Gly Phe Pro Leu Pro Leu Pro Ala Tyr Ile Gln Leu Ser Asn
    450                 455                 460
Leu Val Leu Gln Pro His Gln Asp Phe Leu Leu Phe Gly Ala Asp Val
465                 470                 475                 480
Arg Tyr Ser

<210> SEQ ID NO 13
<211> LENGTH: 427
<212> TYPE: PRT
<213> ORGANISM: Homo sapiens

<400> SEQUENCE: 13

Lys Arg Ile Lys Ile Pro Asp Tyr Ser Asp Ser Phe Lys Ile Lys His
1               5                   10                  15
Leu Gly Lys Gly His Tyr Ser Phe Tyr Ser Met Asp Ile Arg Glu Phe
            20                  25                  30
Gln Leu Pro Ser Ser Gln Ile Ser Met Val Pro Asn Val Gly Leu Lys
        35                  40                  45
Phe Ser Ile Ser Asn Ala Asn Ile Lys Ile Ser Gly Lys Trp Lys Ala
    50                  55                  60
Gln Lys Arg Phe Leu Lys Met Ser Gly Asn Phe Asp Leu Ser Ile Glu
65                  70                  75                  80
Gly Met Ser Ile Ser Ala Asp Leu Lys Leu Gly Ser Asn Pro Thr Ser
                85                  90                  95
Gly Lys Pro Thr Ile Thr Cys Ser Cys Ser Ser His Ile Asn Ser
            100                 105                 110
Val His Val His Ile Ser Lys Ser Lys Val Gly Trp Leu Ile Gln Leu
        115                 120                 125
Phe His Lys Lys Ile Glu Ser Ala Leu Arg Asn Lys Met Asn Ser Gln
    130                 135                 140
Val Cys Glu Lys Val Thr Asn Ser Val Ser Ser Lys Leu Gln Pro Tyr
```

```
                145                 150                 155                 160
Phe Gln Thr Leu Pro Val Met Thr Lys Ile Asp Ser Val Ala Gly Ile
                    165                 170                 175
Asn Tyr Gly Leu Val Ala Pro Ala Thr Thr Ala Glu Thr Leu Asp
                180                 185                 190
Val Gln Met Lys Gly Glu Phe Tyr Ser Glu Asn His His Asn Pro Pro
            195                 200                 205
Pro Phe Ala Pro Pro Val Met Glu Phe Pro Ala Ala His Asp Arg Met
        210                 215                 220
Val Tyr Leu Gly Leu Ser Asp Tyr Phe Asn Thr Ala Gly Leu Val
225                 230                 235                 240
Tyr Gln Glu Ala Gly Val Leu Lys Met Thr Leu Arg Asp Asp Met Ile
                245                 250                 255
Pro Lys Glu Ser Lys Phe Arg Leu Thr Thr Lys Phe Phe Gly Thr Phe
                260                 265                 270
Leu Pro Glu Val Ala Lys Lys Phe Pro Asn Met Lys Ile Gln Ile His
            275                 280                 285
Val Ser Ala Ser Thr Pro Pro His Leu Ser Val Gln Pro Thr Gly Leu
        290                 295                 300
Thr Phe Tyr Pro Ala Val Asp Val Gln Ala Phe Ala Val Leu Pro Asn
305                 310                 315                 320
Ser Ser Leu Ala Ser Leu Phe Leu Ile Gly Met His Thr Thr Gly Ser
                325                 330                 335
Met Glu Val Ser Ala Glu Ser Asn Arg Leu Val Gly Glu Leu Lys Leu
                340                 345                 350
Asp Arg Leu Leu Leu Glu Leu Lys His Ser Asn Ile Gly Pro Phe Pro
            355                 360                 365
Val Glu Leu Leu Gln Asp Ile Met Asn Tyr Ile Val Pro Ile Leu Val
        370                 375                 380
Leu Pro Arg Val Asn Glu Lys Leu Gln Lys Gly Phe Pro Leu Pro Thr
385                 390                 395                 400
Pro Ala Arg Val Gln Leu Tyr Asn Val Val Leu Gln Pro His Gln Asn
                405                 410                 415
Phe Leu Leu Phe Gly Ala Asp Val Val Tyr Lys
            420                 425

<210> SEQ ID NO 14
<211> LENGTH: 477
<212> TYPE: PRT
<213> ORGANISM: Homo sapiens

<400> SEQUENCE: 14

Met Gly Ala Leu Ala Arg Ala Leu Pro Ser Ile Leu Leu Ala Leu Leu
1               5                   10                  15
Leu Thr Ser Thr Pro Glu Ala Leu Gly Ala Asn Pro Gly Leu Val Ala
                20                  25                  30
Arg Ile Thr Asp Lys Gly Leu Gln Tyr Ala Ala Gln Glu Gly Leu Leu
            35                  40                  45
Ala Leu Gln Ser Glu Leu Leu Arg Ile Thr Leu Pro Asp Phe Thr Gly
        50                  55                  60
Asp Leu Arg Ile Pro His Val Gly Arg Gly Arg Tyr Glu Phe His Ser
65                  70                  75                  80
Leu Asn Ile His Ser Cys Glu Leu Leu His Ser Ala Leu Arg Pro Val
                85                  90                  95
```

-continued

Pro Gly Gln Gly Leu Ser Leu Ser Ile Ser Asp Ser Ser Ile Arg Val
            100                 105                 110
Gln Gly Arg Trp Lys Val Arg Lys Ser Phe Phe Lys Leu Gln Gly Ser
            115                 120                 125
Phe Asp Val Ser Val Lys Gly Ile Ser Ile Ser Val Asn Leu Leu Leu
130                 135                 140
Gly Ser Glu Ser Ser Gly Arg Pro Thr Gly Tyr Cys Leu Ser Cys Ser
145                 150                 155                 160
Ser Asp Ile Ala Asp Val Glu Val Asp Met Ser Gly Asp Ser Gly Trp
            165                 170                 175
Leu Leu Asn Leu Phe His Asn Gln Ile Glu Ser Lys Phe Gln Lys Val
            180                 185                 190
Leu Glu Ser Arg Ile Cys Glu Met Ile Gln Lys Ser Val Ser Ser Asp
            195                 200                 205
Leu Gln Pro Tyr Leu Gln Thr Leu Pro Val Thr Thr Glu Ile Asp Ser
            210                 215                 220
Phe Ala Asp Ile Asp Tyr Ser Leu Val Glu Ala Pro Arg Ala Thr Ala
225                 230                 235                 240
Gln Met Leu Glu Val Met Phe Lys Gly Glu Ile Phe His Arg Asn His
            245                 250                 255
Arg Ser Pro Val Thr Leu Leu Ala Ala Ala Glu Glu His Asn Lys Met
            260                 265                 270
Val Tyr Phe Ala Ile Ser Asp Tyr Val Phe Asn Thr Ala Ser Leu Val
            275                 280                 285
Tyr His Glu Glu Gly Tyr Leu Asn Phe Ser Ile Thr Asp Asp Met Ile
            290                 295                 300
Pro Pro Asp Ser Asn Ile Arg Leu Thr Thr Lys Ser Phe Arg Pro Phe
305                 310                 315                 320
Val Pro Arg Leu Ala Arg Leu Tyr Pro Asn Met Asn Leu Glu Leu Gln
            325                 330                 335
Gly Ser Val Pro Ser Ala Pro Leu Leu Ser Val Gln Pro Thr Gly Leu
            340                 345                 350
Thr Phe Tyr Pro Ala Val Asp Val Gln Ala Phe Ala Val Leu Pro Asn
            355                 360                 365
Ser Ser Leu Ala Ser Leu Phe Leu Ile Gly Met His Thr Thr Gly Ser
            370                 375                 380
Met Glu Val Ser Ala Glu Ser Asn Arg Leu Val Gly Glu Leu Lys Leu
385                 390                 395                 400
Asp Arg Leu Leu Val Glu Leu Lys Glu Ser Lys Val Gly Leu Phe Asn
            405                 410                 415
Ala Glu Leu Leu Glu Ala Leu Leu Asn Tyr Tyr Ile Leu Asn Thr Leu
            420                 425                 430
Tyr Pro Lys Phe Asn Asp Lys Leu Ala Glu Gly Phe Pro Leu Pro Leu
            435                 440                 445
Leu Lys Arg Val Gln Leu Tyr Asp Leu Gly Leu Gln Ile His Lys Asp
            450                 455                 460
Phe Leu Phe Leu Gly Ala Asn Val Gln Tyr Met Arg Val
465                 470                 475

<210> SEQ ID NO 15
<211> LENGTH: 493
<212> TYPE: PRT
<213> ORGANISM: Homo sapiens

<400> SEQUENCE: 15

-continued

```
Met Val Leu Leu Trp Ala Leu Phe Leu Ala Leu Leu Ala Gly Ala His
1               5                   10                  15

Ala Glu Leu Pro Gly Cys Lys Ile Arg Val Thr Ser Ala Ala Leu Asp
                20                  25                  30

Leu Val Lys Gln Glu Gly Leu Arg Phe Leu Glu Gln Glu Leu Glu Thr
            35                  40                  45

Ile Thr Ile Pro Asp Val Tyr Gly Ala Lys Gly His Phe Tyr Tyr Asn
        50                  55                  60

Ile Ser Asp Val Arg Val Thr Gln Leu His Leu Ile Ser Ser Glu Leu
65                  70                  75                  80

His Phe Gln Pro Asp Gln Asp Leu Leu Leu Asn Ile Ser Asn Ala Ser
                85                  90                  95

Leu Gly Leu His Phe Arg Arg Gln Leu Leu Tyr Trp Phe Leu Tyr Asp
                100                 105                 110

Gly Gly Tyr Ile Asn Ala Ser Ala Glu Gly Val Ser Ile Arg Thr Gly
            115                 120                 125

Leu Gln Leu Ser Gln Asp Ser Ser Gly Arg Ile Lys Val Ser Asn Val
130                 135                 140

Ser Cys Glu Ala Ser Val Ser Lys Met Asn Met Ala Phe Gly Gly Thr
145                 150                 155                 160

Phe Arg Arg Met Tyr Asn Phe Phe Ser Thr Phe Ile Thr Ser Gly Met
                165                 170                 175

Arg Phe Leu Leu Asn Gln Gln Ile Cys Pro Val Leu Tyr His Ala Gly
            180                 185                 190

Thr Val Leu Leu Asn Ser Leu Leu Asp Thr Val Pro Val Arg Ser Ser
            195                 200                 205

Val Asp Asp Leu Val Gly Ile Asp Tyr Ser Leu Leu Lys Asp Pro Val
        210                 215                 220

Val Ser Asn Gly Asn Leu Asp Met Glu Phe Arg Gly Ala Phe Phe Pro
225                 230                 235                 240

Leu Lys Glu Asp Asn Trp Ser Leu Pro Asn Arg Ala Val Glu Pro Gln
                245                 250                 255

Leu Glu Asp Asp Glu Arg Met Val Tyr Val Ala Phe Ser Glu Phe Phe
            260                 265                 270

Phe Asp Ser Ala Met Glu Ser Tyr Phe Gln Ala Gly Ala Leu Gln Leu
        275                 280                 285

Thr Leu Val Gly Asp Lys Val Pro Ser Asp Leu Asp Met Leu Leu Arg
        290                 295                 300

Ala Thr Tyr Phe Gly Ser Ile Val Leu Leu Ser Pro Thr Val Ile Asn
305                 310                 315                 320

Ser Pro Leu Lys Leu Lys Leu Glu Ala Thr Ser Pro Arg Cys Thr
                325                 330                 335

Ile Lys Pro Ser Gly Thr Thr Ile Ser Ile Thr Ala Ser Val Thr Ile
            340                 345                 350

Thr Leu Ala Pro Pro Met Leu Pro Glu Val Glu Leu Ser Lys Met Ile
        355                 360                 365

Met Glu Gly Arg Leu Ser Ala Lys Leu Thr Leu Arg Gly Lys Ala Leu
        370                 375                 380

Arg Val Lys Leu Asp Leu Arg Arg Phe Gln Ile Tyr Ser Asn Gln Ser
385                 390                 395                 400

Ala Leu Glu Ser Leu Ala Leu Ile Pro Leu Gln Ala Pro Leu Lys Thr
                405                 410                 415
```

-continued

Leu Leu Gln Ile Gly Val Met Pro Leu Leu Asn Glu Arg Thr Trp Arg
            420                 425                 430

Gly Val Gln Ile Pro Leu Pro Glu Gly Ile Asn Phe Val Arg Glu Val
            435                 440                 445

Val Thr Asn His Ala Gly Phe Val Thr Val Gly Ala Asp Leu His Phe
        450                 455                 460

Ala Lys Gly Leu Arg Glu Val Ile Asp Lys Asn Arg Pro Ala Asp Val
465                 470                 475                 480

Ala Ala Ser His Val Pro Pro Ser Ala Ala Ala
                485                 490

<210> SEQ ID NO 16
<211> LENGTH: 476
<212> TYPE: PRT
<213> ORGANISM: Homo sapiens

<400> SEQUENCE: 16

Met Leu Ala Ala Thr Val Leu Thr Leu Ala Leu Leu Gly Asn Ala His
1               5                   10                  15

Ala Cys Ser Lys Gly Thr Ser His Glu Ala Gly Ile Val Cys Arg Ile
            20                  25                  30

Thr Lys Pro Ala Leu Leu Val Leu Asn His Glu Thr Ala Lys Val Ile
        35                  40                  45

Gln Thr Ala Phe Gln Arg Ala Ser Tyr Pro Asp Ile Thr Gly Glu Lys
    50                  55                  60

Ala Met Met Leu Leu Gly Gln Val Lys Tyr Gly Leu His Asn Ile Gln
65                  70                  75                  80

Ile Ser His Leu Ser Ile Ala Ser Ser Gln Val Glu Leu Val Glu Ala
                85                  90                  95

Lys Ser Ile Asp Val Ser Ile Gln Asn Val Ser Val Val Phe Lys Gly
            100                 105                 110

Thr Leu Lys Tyr Gly Tyr Thr Thr Ala Trp Trp Leu Gly Ile Asp Gln
        115                 120                 125

Ser Ile Asp Phe Glu Ile Asp Ser Ala Ile Asp Leu Gln Ile Asn Thr
    130                 135                 140

Gln Leu Thr Cys Asp Ser Gly Arg Val Arg Thr Asp Ala Pro Asp Cys
145                 150                 155                 160

Tyr Leu Ser Phe His Lys Leu Leu His Leu Gln Gly Glu Arg Glu
                165                 170                 175

Pro Gly Trp Ile Lys Gln Leu Phe Thr Asn Phe Ile Ser Phe Thr Leu
            180                 185                 190

Lys Leu Val Leu Lys Gly Gln Ile Cys Lys Glu Ile Asn Val Ile Ser
        195                 200                 205

Asn Ile Met Ala Asp Phe Val Gln Thr Arg Ala Ala Ser Ile Leu Ser
    210                 215                 220

Asp Gly Asp Ile Gly Val Asp Ile Ser Leu Thr Gly Asp Pro Val Ile
225                 230                 235                 240

Thr Ala Ser Tyr Leu Glu Ser His His Lys Gly His Phe Ile Tyr Lys
                245                 250                 255

Asn Val Ser Glu Asp Leu Pro Leu Pro Thr Phe Ser Pro Thr Leu Leu
            260                 265                 270

Gly Asp Ser Arg Met Leu Tyr Phe Trp Phe Ser Glu Arg Val Phe His
        275                 280                 285

Ser Asp Glu Phe Lys Ala Val Leu Glu Thr Trp Gly Phe Asn Thr Asn
    290                 295                 300

```
Gln Glu Ile Phe Gln Glu Val Val Gly Gly Phe Pro Ser Gln Ala Gln
305                 310                 315                 320

Val Thr Val His Cys Leu Lys Met Pro Lys Ile Ser Cys Gln Asn Lys
            325                 330                 335

Gly Val Val Val Asn Ser Ser Val Met Val Lys Phe Leu Phe Pro Arg
            340                 345                 350

Pro Asp Gln Gln His Ser Val Ala Tyr Thr Phe Glu Glu Asp Ile Val
            355                 360                 365

Thr Thr Val Gln Ala Ser Tyr Ser Lys Lys Lys Leu Phe Leu Ser Leu
        370                 375                 380

Leu Asp Phe Gln Ile Thr Pro Lys Thr Val Ser Asn Leu Thr Glu Ser
385                 390                 395                 400

Ser Ser Glu Ser Ile Gln Ser Phe Leu Gln Ser Met Ile Thr Ala Val
                405                 410                 415

Gly Ile Pro Glu Val Met Ser Arg Leu Glu Val Val Phe Thr Ala Leu
            420                 425                 430

Met Asn Ser Lys Gly Val Ser Leu Phe Asp Ile Ile Asn Pro Glu Ile
            435                 440                 445

Ile Thr Arg Asp Gly Phe Leu Leu Leu Gln Met Asp Phe Gly Phe Pro
        450                 455                 460

Glu His Leu Leu Val Asp Phe Leu Gln Ser Leu Ser
465                 470                 475
```

GENETIC MARKERS FOR IMPROVED DISEASE RESISTANCE IN ANIMALS (BPI)

CROSS-REFERENCE TO RELATED APPLICATIONS

This application claims benefit under 35 U.S.C. § 119(e) of provisional application 60/294,668 filed May 31, 2001.

GRANT REFERENCE

Work for this invention was funded in part by ISU Grant No. 400-43-71-21-3337. The Government may have certain rights in this invention.

FIELD OF THE INVENTION

This invention relates generally to the detection of genetic differences among animals. More particularly, the invention relates to genetic markers which have been identified in several genes indicative of heritable phenotypes associated with improved traits, such as disease resistance or performance. Methods and compositions for use of these markers in genotyping of animals and selection are also disclosed.

BACKGROUND OF THE INVENTION

Genetic differences exist among individual animals as well as among breeds which can be exploited by breeding techniques to achieve animals with desirable characteristics. For example, Chinese pig breeds are known for reaching puberty at an early age and for their large litter size, while American breeds are known for their greater growth rates and leanness. Often, however, heritability for desired traits is low, and standard breeding methods which select individuals based upon phenotypic variations do not take fully into account genetic variability or complex gene interactions which exist.

There is a continuing need for an approach that deals with selection for disease resistance at the cellular or DNA level. This method will provide the ability to genetically evaluate animals and to enable breeders to more accurately select those animals which not only phenotypically express desirable traits but those which express favorable underlying genetic criteria. This has largely been accomplished to date by marker-assisted selection.

RFLP analysis has been used by several groups to study pig DNA. Jung et al., Theor. Appl. Genet., 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., Abstract for Annual Meeting of Midwestern Section of the American Society of Animal Science, Mar. 26–28, 1990, incorporated herein by reference, reports on the polymorphism of swine major histocompatibility complex (MHC) genes for Chinese pigs, also demonstrated by RFLP analysis. Jung et al. Animal Genetics, 26:79–91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves a novel and lengthy process of the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established, selection decisions could be made very easily, since DNA markers can be assayed any time after a tissue or blood sample can be collected from the individual infant animal, or even an embryo.

The use of genetic differences in receptor genes has become a valuable marker system for selection. For example, U.S. Pat. Nos. 5,550,024 and 5,374,526, issued to Rothschild et al., disclose a polymorphism in the pig estrogen receptor gene which is associated with larger litter size, the disclosure of which is incorporated herein by reference. U.S. Pat. No. 5,935,784 discloses polymorphic markers in the pig prolactin receptor gene which are associated with larger litter size and overall reproductive efficiency, the disclosure of which is incorporated herein by reference.

The present invention provides a genetic markers, based upon the discovery of a polymorphisms in the porcine BPI gene, which correlate with resistance or susceptibility to pathogenic infection in pigs. This will permit genetic typing of pigs for their BPI allele and for determination of the relationship of specific RFLPs to resistance to infection. It will also permit the identification of individual males and females that carry the gene for improved resistance. Thus, the markers may be selection tools in breeding programs to develop lines and breeds that produce litters containing more resistant offspring. Also disclosed are novel porcine BPIP genomic sequences, as well as primers for assays to identify the presence or absence of marker alleles.

According to the invention a polymorphism was identified in the BPI gene which is associated with the improved resistance to pathogenic infection.

It is an object of the invention to provide a method of screening pigs to determine those more likely to produce offspring with improved pathogenic resistance, in the BPI gene.

Another object of the invention is to provide a method for identifying genetic markers for improved disease resistance.

A further object of the invention is to provide genetic markers for selection and breeding to obtain pigs that will be expected to have a lower susceptibility to infection than those without the favorable allele.

Yet another object of the invention is to provide a kit for evaluating a sample of pig DNA for specific genetic markers of disease resistance.

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

SUMMARY OF THE INVENTION

To achieve the objects and in accordance with the purpose of the invention, as embodied and broadly described herein, the present invention provides a method for screening animals to determine those more likely to have beneficial phenotypes or against those with deleterious phenotypes (such as, or associated with, improved innate immunity, disease resistance or resistance to bacterial infection, as evidenced by bacterial count, lymphocyte count, neutrophil count, or monocyte count after challenge to identify animals which have superior bacterial killing, or ability to stave off infection in a particular population, when bred, or raised or to select against pigs which have alleles indicating unfavorable phenotypes. These traits may also be observed by assaying general indicia of overall health of the animal. As used herein the term "biologically different disease resistance" or "innate immunity" shall mean an ability to stave off infection that is superior to that which is observed when the favorable allele is not present as evidenced by indicia including but not limited to average lymphocyte count and percentage, monocyte count, neutrophil count and percentage and bacterial count after challenge or other measurements of innate immunity as well as measurements of overall health of the animal such as feed intake, weight gain and the like.

Thus, the present invention provides a method for screening pigs to determine those more likely to have the improved trait of superior disease resistance and/or those less likely to demonstrate those traits which method comprises the steps: 1) obtaining a sample of tissue or genomic DNA from an animal; and 2) analyzing the mRNA or genomic DNA obtained in 1) to determine which allele(s) is/are present. Briefly, the sample of genetic material analyzed to determine the presence or absence of a particular allele that is correlated with a desirable trait, or one which is linked thereto.

As is well known to those of skill in the art, a variety of techniques may be utilized when comparing nucleic acid molecules for sequence differences. These include by way of example, restriction fragment length polymorphism analysis, heteroduplex analysis, single strand conformation polymorphism analysis, denaturing gradient electrophoresis and temperature gradient electrophoresis.

In one embodiment, the polymorphism is a restriction fragment length polymorphism and the assay comprises identifying the gene from isolated genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from an animal gene that is either known to have or not to have the desired marker. If an animal tests positive for the marker (or allele), such animal can be considered for inclusion in the breeding program. If the animal does not test positive for the marker genotype, the animal can be culled from the group and otherwise used.

In a most preferred embodiment, the gene, or a fragment thereof, is isolated by the use of primers and DNA polymerase to amplify a specific region of the gene which contains the polymorphism or a polymorphism linked thereto. Next, the amplified region is either directly separated or sequenced or is digested with a restriction enzyme and fragments are again separated. Visualization of the separated fragments, or RFLP pattern, is by simple staining of the fragments, or by labeling the primers or the nucleoside triphosphates used in amplification.

In another embodiment, the invention comprises a method for identifying a genetic marker for disease resistance traits, such as bacterial counts, lymphocyte count, neutrophil count, or monocyte count after challenge. Male and female animals of the same breed, breed cross, or similar genetic lineage are bred, and the disease resistance traits are determined. A polymorphism in the gene of each animal is identified and associated with the desired trait(s). Preferably, PCR-RFLP analysis is used to determine the polymorphism.

It is also possible to establish linkage between specific alleles of alternative DNA markers and alleles of DNA markers known to be associated with a particular gene (e.g., the BPI gene discussed herein) which have previously been shown to be associated with a particular trait. Thus, in the present situation, taking a particular gene, it would be possible, at least in the short term, to select for pigs, or other animals, likely to have superior disease resistance or ability to stave off infection, or alternatively, against pigs likely to have inferior traits, indirectly, by selecting for certain alleles of a particular gene associated with the marker alleles through the selection of specific linked alleles of alternative chromosome markers. Thus, in the present situation, taking the BPI gene, it would be possible, at least in the short term, to select for pigs likely to produce disease resistance, or alternatively, against pigs likely to produce susceptible litters indirectly, by selecting for certain alleles of the BPI associated marker through the selection of specific alleles of alternative markers located on the same chromosome BPI is.

The invention further comprises a kit for evaluating a sample of DNA for the presence in genetic material of a desired genetic marker located in the gene indicative of a inheritable trait of disease resistance or ability to stave off infection. At a minimum, the kit is a container with one or more reagents that identify a polymorphism in the porcine BPI gene. Preferably, the reagent is a set of oligonucleotide primers capable of amplifying a fragment of the selected gene that contains a polymorphism. Preferably, the kit further contains a restriction enzyme that cleaves the gene in at least one place, allowing for separation of fragments and detection of polymorphic loci.

In another embodiment, the invention comprises a method for identifying a genetic marker for meat quality and/or growth in a particular population. Male and female pigs of the same breed or breed cross or similar genetic lineage are bred, and meat quality and/or growth produced by each pig is determined. A polymorphism in the BPI gene of each pig is identified and associated with the meat quality and/or growth. Preferably, RFLP analysis is used to determine the polymorphism.

In another embodiment, the invention comprises a method for identifying a genetic marker for meat quality and/or growth in any particular economic animal other than a pig. Based upon the highly conserved nature of this gene among different animals and the location of the polymorphisms within these highly conserved regions, is it expected that with no more than routine testing as described herein this marker can be applied to different animal species to select for meat quality and/or growth based on the teachings herein. Male and female animals of the same breed or breed cross or similar genetic lineage are bred, and the meat quality and/or growth produced by each animal is determined and correlated. For other animals in which sequences are available a BLAST comparison of sequences may be used to ascertain whether the particular allele is analogous to the one disclosed herein. The analogous polymorphism will be present in other animals and in other closely related genes. The term "analogous polymorphism" shall be a polymorphism which is the same as any of those disclosed herein as determined by BLAST comparisons.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. In this case the Reference BPI sequence. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237–244 (1988); Higgins and Sharp, CABIOS 5:151–153 (1989); Corpet, et al., Nucleic Acids Research 16:10881–90 (1988); Huang, et al., Computer Applications in the Biosciences 8:155–65 (1992), and Pearson, et al., Methods in Molecular Biology 24:307–331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et a., Nucleic Acids Res. 25:3389–3402 (1997). Software for performing BLAST analyses is publicly available, e.g., through the National Center for Biotechnology-Information (http://www.ncbi.nlm.nih.gov/).

This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17:149–163 (1993)) and XNU (Clayerie and States, Comput. Chem., 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e)(I) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or preferably at least 70%, 80%, 90%, and most preferably at least 95%.

These programs and algorithms can ascertain the analogy of a particular polymorphism in a target gene to those disclosed herein. It is expected that this polymorphism will exist in other animals and use of the same in other animals than disclosed herein involved no more than routine optimization of parameters using the teachings herein.

It is also possible to establish linkage between specific alleles of alternative DNA markers and alleles of DNA markers known to be associated with a particular gene (e.g. the BPI gene discussed herein), which have previously been shown to be associated with a particular trait. Thus, in the present situation, taking the BPI gene, it would be possible, at least in the short term, to select for pigs likely to produce a desired meat quality and/or growth, or alternatively against pigs likely to produce less desirable meat quality and/or growth, indirectly, by selecting for certain alleles of a BPI associated marker through the selection of specific alleles of alternative chromosome markers. As used herein the term "genetic marker" shall include not only the polymorphism disclosed by any means of assaying for the protein changes associated with the polymorphism, be they linked markers, use of microsatellites, or even other means of assaying for the causative protein changes indicated by the marker and the use of the same to influence the meat quality and/or growth of an animal.

As used herein, often the designation of a particular polymorphism is made by the name of a particular restriction enzyme. This is not intended to imply that the only way that the site can be identified is by the use of that restriction enzyme. There are numerous databases and resources available to those of skill in the art to identify other restriction enzymes which can be used to identify a particular polymorphism, for example http://darwin.bio.geneseo.edu which can give restriction enzymes upon analysis of a sequence and the polymorphism to be identified. In fact as disclosed in the teachings herein there are numerous ways of identifying a particular polymorphism or allele with alternate methods which may not even include a restriction enzyme, but which assay for the same genetic or proteomic alternative form.

In yet another embodiment of this invention novel porcine nucleotide sequences have been identified and are disclosed which encode porcine BPI. The cDNA of the porcine BPI gene as well as some intronic DNA sequences are disclosed. These sequences may be used for the design of primers to assay for the SNP's of the invention or for production of recombinant BPI. The invention is intended to include these sequences as well as all conservatively modified variants thereof as well as those sequences which will hybridize under conditions of high stringency to the sequences disclosed. The term BPI as used herein shall be interpreted to include these conservatively modified variants as well as those hybridized sequences.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);

5) Isoleucine (I), Leucine (L), Methionine (M), Valine (V); and

6) Phenylalanine (F), Tyrosine (Y), Tryptophan (W).

See also, Creighton (1984) Proteins W.H. Freeman and Company.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate *Macronucleus*, may be used when the nucleic acid is expressed therein.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$) Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory* Techniques in Biochemistry and Molecular Biology-Hybridization with Nucleic Acids Probes, Part I, Chapter 2, Ausubel, et al., Eds., Greene Publishing and Wiley-Interscience, New York (1995).

DETAILED DESCRIPTION FO THE FIGURES

FIG. 1 is the sequence (SEQ ID NO:3) of the region amplified by primers 1 and 2. Bold text are exon 4 sequences and regular text are intron sequences. R=A or G. Ava II polymorphism is at position 103.

FIG. 2 is the sequence (SEQ ID NO:6) of the region amplified by primers 3 and 4. Bold text are exon 10 sequences and regular text are intron sequences, K=G or T.

FIG. 3 is the sequence (SEQ ID NO:8) amplified by primers 7 and 8. Bold text are exon 10 and exon 11 sequences and regular text are intron sequences, ☐ represents about 300 bp insertion present in alternate allele. This inserted sequence is a repetitive region that is difficult to sequence accurately.

FIGS. 4(*a–c*) and 5(*a–b*) are a comparison of the full length coding region sequence of porcine BPI and alignment of full-length sequence of each allele (3,4) at the DNA level (4) and the protein level (5). Differences in base pair sequence are in bold and underlined. 1 porcine a3 (SEQ ID NO: 11); 2 porcine a4 (SEQ ID NO:12); 3 human BPI (SEQ ID NO:13); 4 human LBP (SEQ ID NO: 14); 5 human PLTP (SEQ ID NO:15); 6 human CETP (SEQ ID NO:16).

DETAILED DESCRIPTION OF THE INVENTION

Reference will now be made in detail to the presently preferred embodiments of the invention, which together with the following examples, serve to explain the principles of the invention. All references cited herein are hereby expressly incorporated by reference.

The invention relates to the identification of quantitative trait loci (QTL) for improved disease resistance or resistance to pathogen infection, including, but not limited to, Salmonellosis, identifiable by traits such as bacterial count, total or specific leukocyte counts (including white blood cells, lymphocytes, monocytes, neutrophils) before and/or after infection, or leukocyte function to identify pigs and other animals which have superior pathogen killing or ability to stave off infection. It provides a method of screening animals to determine those more likely to have improved resistance and/or good immune system and overall health traits (as shown by measures such as weight gain or feed efficiency) when bred by identifying the presence or an absence of a polymorphism in certain genes (BPI) that are correlated with these traits.

In one embodiment the invention relates to novel BPI alleles characterized by a polymorphisms in exon 4, intron 10 and exon 10 which are correlated with improved disease resistance and/or innate immunity. The presence a particular allele may be identified in one embodiment by the use of the restriction enzymes Ava II or Hpa II.

Thus, the invention relates to genetic markers and methods of identifying those markers in a pig or other animal of a particular breed, strain, population, or group, whereby an animal has disease resistance above the mean for that particular breed, strain, population, or group.

The marker may be identified by any method known to one of ordinary skill in the art which identifies the presence or absence of the particular allele or marker, including, for example, direct sequencing single-strand conformation polymorphism analysis (SSCP), base excision sequence scanning (BESS), RFLP analysis, heteroduplex analysis, denaturing gradient gel electrophoresis, allelic PCR, temperature gradient electrophoresis, ligase chain reaction, direct sequencing, minisequencing, nucleic acid hybridization, and micro-array-type detection of the BPI gene, or other linked sequences, and examination for a polymorphic site. Yet another technique includes an Invader Assay which includes isothermic amplification that relies on a catalytic release of fluorescence. See Third Wave Technology at www.twt.com. All of these techniques are intended to be within the scope of the invention. The markers may also be assayed for by identifying correlating changes in amino acids encoded by the sequences herein.

A Brief Description of these Techniques Follows.

Isolation and Amplification of Nucleic Acid

Samples of patient, proband, test subject, or family member genomic DNA are isolated from any convenient source including saliva, buccal cells, hair roots, blood, cord blood, amniotic fluid, interstitial fluid, peritoneal fluid, chorionic villus, and any other suitable cell or tissue sample with intact interphase nuclei or metaphase cells. The cells can be obtained from solid tissue as from a fresh or preserved organ or from a tissue sample or biopsy. The sample can contain compounds which are not naturally intermixed with the biological material such as preservatives, anticoagulants, buffers, fixatives, nutrients, antibiotics, or the like.

Methods for isolation of genomic DNA from these various sources are described in, for example, Kirby, DNA Fingerprinting, An Introduction, W. H. Freeman & Co. New York (1992). Genomic DNA can also be isolated from cultured primary or secondary cell cultures or from transformed cell lines derived from any of the aforementioned tissue samples.

Samples of patient, proband, test subject or family member RNA can also be used. RNA can be isolated from tissues expressing the BPI gene as described in Sambrook et al., supra. RNA can be total cellular RNA, mRNA, poly A+ RNA, or any combination thereof. For best results, the RNA is purified, but can also be unpurified cytoplasmic RNA. RNA can be reverse transcribed to form DNA which is then used as the amplification template, such that the PCR indirectly amplifies a specific population of RNA transcripts. See, e.g., Sambrook, supra, Kawasaki et al., Chapter 8 in PCR Technology, (1992) supra, and Berg et al., Hum. Genet. 85:655–658 (1990).

PCR Amplification

The most common means for amplification is polymerase chain reaction (PCR), as described in U.S. Pat. Nos. 4,683,195, 4,683,202, 4,965,188 each of which is hereby incorporated by reference. If PCR is used to amplify the target regions in blood cells, heparinized whole blood should be drawn in a sealed vacuum tube kept separated from other samples and handled with clean gloves. For best results, blood should be processed immediately after collection; if this is impossible, it should be kept in a sealed container at 4° C. until use. Cells in other physiological fluids may also be assayed. When using any of these fluids, the cells in the fluid should be separated from the fluid component by centrifugation.

Tissues should be roughly minced using a sterile, disposable scalpel and a sterile needle (or two scalpels) in a 5 mm Petri dish. Procedures for removing paraffin from tissue sections are described in a variety of specialized handbooks well known to those skilled in the art.

To amplify a target nucleic acid sequence in a sample by PCR, the sequence must be accessible to the components of the amplification system. One method of isolating target DNA is crude extraction which is useful for relatively large samples. Briefly, mononuclear cells from samples of blood, amniocytes from amniotic fluid, cultured chorionic villus cells, or the like are isolated by layering on sterile Ficoll-Hypaque gradient by standard procedures. Interphase cells are collected and washed three times in sterile phosphate buffered saline before DNA extraction. If testing DNA from peripheral blood lymphocytes, an osmotic shock (treatment of the pellet for 10 sec with distilled water) is suggested, followed by two additional washings if residual red blood cells are visible following the initial washes. This will prevent the inhibitory effect of the heme group carried by hemoglobin on the PCR reaction. If PCR testing is not performed immediately after sample collection, aliquots of $10^6$ cells can be pelleted in sterile Eppendorf tubes and the dry pellet frozen at −20° C. until use.

The cells are resuspended ($10^6$ nucleated cells per 100 µl) in a buffer of 50 mM Tris-HCl (pH 8.3), 50 mM KCl 1.5 mM $MgCl_2$, 0.5% Tween 20, 0.5% NP40 supplemented with 100 µg/ml of proteinase K. After incubating at 56° C. for 2 hr. the cells are heated to 95° C. for 10 min to inactivate the proteinase K and immediately moved to wet ice (snap-cool). If gross aggregates are present, another cycle of digestion in the same buffer should be undertaken. Ten µl of this extract is used for amplification.

When extracting DNA from tissues, e.g., chorionic villus cells or confluent cultured cells, the amount of the above mentioned buffer with proteinase K may vary according to the size of the tissue sample. The extract is incubated for 4–10 hrs at 50°–60° C. and then at 95° C. for 10 minutes to inactivate the proteinase. During longer incubations, fresh proteinase K should be added after about 4 hr at the original concentration.

When the sample contains a small number of cells, extraction may be accomplished by methods as described in Higuchi, "Simple and Rapid Preparation of Samples for PCR", in PCR Technology, Ehrlich, H. A. (ed.), Stockton Press, New York, which is incorporated herein by reference. PCR can be employed to amplify target regions in very small numbers of cells (1000–5000) derived from individual colonies from bone marrow and peripheral blood cultures. The cells in the sample are suspended in 20 μl of PCR lysis buffer (10 mM Tris-HCl (pH 8.3), 50 mM KCl, 2.5 mM MgCl$_2$, 0.1 mg/ml gelatin, 0.45% NP40, 0.45% Tween 20) and frozen until use. When PCR is to be performed, 0.6 μl of proteinase K (2 mg/ml) is added to the cells in the PCR lysis buffer. The sample is then heated to about 60° C. and incubated for 1 hr. Digestion is stopped through inactivation of the proteinase K by heating the samples to 95° C. for 10 min and then cooling on ice.

A relatively easy procedure for extracting DNA for PCR is a salting out procedure adapted from the method described by Miller et al., Nucleic Acids Res. 16:1215 (1988), which is incorporated herein by reference. Mononuclear cells are separated on a Ficoll-Hypaque gradient. The cells are resuspended in 3 ml of lysis buffer (10 mM Tris-HCl, 400 mM NaCl, 2 mM Na$_2$ EDTA, pH 8.2). Fifty μl of a 20 mg/ml solution of proteinase K and 150 μl of a 20% SDS solution are added to the cells and then incubated at 37° C. overnight. Rocking the tubes during incubation will improve the digestion of the sample. If the proteinase K digestion is incomplete after overnight incubation (fragments are still visible), an additional 50 μl of the 20 mg/ml proteinase K solution is mixed in the solution and incubated for another night at 37° C. on a gently rocking or rotating platform. Following adequate digestion, one ml of a 6M NaCl solution is added to the sample and vigorously mixed. The resulting solution is centrifuged for 15 minutes at 3000 rpm. The pellet contains the precipitated cellular proteins, while the supernatant contains the DNA. The supernatant is removed to a 15 ml tube that contains 4 ml of isopropanol. The contents of the tube are mixed gently until the water and the alcohol phases have mixed and a white DNA precipitate has formed. The DNA precipitate is removed and dipped in a solution of 70% ethanol and gently mixed. The DNA precipitate is removed from the ethanol and air-dried. The precipitate is placed in distilled water and dissolved.

Kits for the extraction of high-molecular weight DNA for PCR include a Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, LaJolla, Calif.), TurboGen Isolation Kit (Invitrogen, San Diego, Calif.), and the like. Use of these kits according to the manufacturer's instructions is generally acceptable for purification of DNA prior to practicing the methods of the present invention.

The concentration and purity of the extracted DNA can be determined by spectrophotometric analysis of the absorbance of a diluted aliquot at 260 nm and 280 nm. After extraction of the DNA, PCR amplification may proceed. The first step of each cycle of the PCR involves the separation of the nucleic acid duplex formed by the primer extension. Once the strands are separated, the next step in PCR involves hybridizing the separated strands with primers that flank the target sequence. The primers are then extended to form complementary copies of the target strands. For successful PCR amplification, the primers are designed so that the position at which each primer hybridizes along a duplex sequence is such that an extension product synthesized from one primer, when separated from the template (complement), serves as a template for the extension of the other primer. The cycle of denaturation, hybridization, and extension is repeated as many times as necessary to obtain the desired amount of amplified nucleic acid.

In a particularly useful embodiment of PCR amplification, strand separation is achieved by heating the reaction to a sufficiently high temperature for a sufficient time to cause the denaturation of the duplex but not to cause an irreversible denaturation of the polymerase (see U.S. Pat. No. 4,965,188, incorporated herein by reference). Typical heat denaturation involves temperatures ranging from about 80° C. to 105° C. for times ranging from seconds to minutes. Strand separation, however, can be accomplished by any suitable denaturing method including physical, chemical, or enzymatic means. Strand separation may be induced by a helicase, for example, or an enzyme capable of exhibiting helicase activity. For example, the enzyme RecA has helicase activity in the presence of ATP. The reaction conditions suitable for strand separation by helicases are known in the art (see Kuhn Hoffman-Berling, 1978, CSH-Quantitative Biology, 43:63–67; and Radding, 1982, Ann. Rev. Genetics 16:405–436, each of which is incorporated herein by reference.

Template-dependent extension of primers in PCR is catalyzed by a polymerizing agent in the presence of adequate amounts of four deoxyribonucleotide triphosphates (typically dATP, dGTP, dCTP, and dTTP) in a reaction medium comprised of the appropriate salts, metal cations, and pH buffering systems. Suitable polymerizing agents are enzymes known to catalyze template-dependent DNA synthesis. In some cases, the target regions may encode at least a portion of a protein expressed by the cell. In this instance, mRNA may be used for amplification of the target region. Alternatively, PCR can be used to generate a cDNA library from RNA for further amplification, the initial template for primer extension is RNA. Polymerizing agents suitable for synthesizing a complementary, copy-DNA (cDNA) sequence from the RNA template are reverse transcriptase (RT), such as avian myeloblastosis virus RT, Moloney murine leukemia virus RT, or *Thermus thermophilus* (Tth) DNA polymerase, a thermostable DNA polymerase with reverse transcriptase activity marketed by Perkin Elmer Cetus, Inc. Typically, the genomic RNA template is heat degraded during the first denaturation step after the initial reverse transcription step leaving only DNA template. Suitable polymerases for use with a DNA template include, for example, *E. coli* DNA polymerase I or its Klenow fragment, T4 DNA polymerase, Tth polymerase, and Taq polymerase, a heat-stable DNA polymerase isolated from *Thermus aquaticus* and commercially available from Perkin Elmer Cetus, Inc. The latter enzyme is widely used in the amplification and sequencing of nucleic acids. The reaction conditions for using Taq polymerase are known in the art and are described in Gelfand, 1989, PCR Technology, supra.

Allele Specific PCR

Allele-specific PCR differentiates between target regions differing in the presence of absence of a variation or polymorphism. PCR amplification primers are chosen which bind only to certain alleles of the target sequence. This method is described by Gibbs, Nucleic Acid Res. 17:12427–2448 (1989).

Allele Specific Oligonucleotide Screening Methods

Further diagnostic screening methods employ the allele-specific oligonucleotide (ASO) screening methods, as described by Saiki et al., Nature 324:163–166 (1986). Oligonucleotides with one or more base pair mismatches are generated for any particular allele. ASO screening methods detect mismatches between variant target genomic: or PCR amplified DNA and non-mutant oligonucleotides, showing decreased binding of the oligonucleotide relative to a mutant oligonucleotide. Oligonucleotide probes can be designed that under low stringency will bind to both polymorphic forms of the allele, but which at high stringency, bind to the allele to which they correspond. Alternatively, stringency conditions can be devised in which an essentially binary response is obtained, i.e., an ASO corresponding to a variant form of the target gene will hybridize to that allele, and not to the wildtype allele.

Ligase Mediated Allele Detection Method

Target regions of a test subject's DNA can be compared with target regions in unaffected and affected family members by ligase-mediated allele detection. See Landegren et al., Science 241:107–1080 (1988). Ligase may also be used to detect point mutations in the ligation amplification reaction described in Wu et al., Genomics 4:560–569 (1989). The ligation amplification reaction (LAR) utilizes amplification of specific DNA sequence using sequential rounds of template dependent ligation as described in Wu, supra, and Barany, Proc. Nat. Acad. Sci. 88:189–193 (1990).

Denaturing Gradient Gel Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution. DNA molecules melt in segments, termed melting domains, under conditions of increased temperature or denaturation. Each melting domain melts cooperatively at a distinct, base-specific melting temperature (TM). Melting domains are at least 20 base pairs in length, and may be up to several hundred base pairs in length.

Differentiation between alleles based on sequence specific melting domain differences can be assessed using polyacrylamide gel electrophoresis, as described in Chapter 7 of Erlich, ed., PCR Technology, Principles and Applications for DNA Amplification, W.H. Freeman and Co., New York (1992), the contents of which are hereby incorporated by reference.

Generally, a target region to be analyzed by denaturing gradient gel electrophoresis is amplified using PCR primers flanking the target region. The amplified PCR product is applied to a polyacrylamide gel with a linear denaturing gradient as described in Myers et al., Meth. Enzymol. 155:501–527 (1986), and Myers et al., in Genomic Analysis, A Practical Approach, K. Davies Ed. IRL Press Limited, Oxford, pp. 95–139 (1988), the contents of which are hereby incorporated by reference. The electrophoresis system is maintained at a temperature slightly below the Tm of the melting domains of the target sequences.

In an alternative method of denaturing gradient gel electrophoresis, the target sequences may be initially attached to a stretch of GC nucleotides, termed a GC clamp, as described in Chapter 7 of Erlich, supra. Preferably, at least 80% of the nucleotides in the GC clamp are either guanine or cytosine. Preferably, the GC clamp is at least 30 bases long. This method is particularly suited to target sequences with high Tm's.

Generally, the target region is amplified by the polymerase chain reaction as described above. One of the oligonucleotide PCR primers carries at its 5' end, the GC clamp region, at least 30 bases of the GC rich sequence, which is incorporated into the 5' end of the target region during amplification. The resulting amplified target region is run on an electrophoresis gel under denaturing gradient conditions as described above. DNA fragments differing by a single base change will migrate through the gel to different positions, which may be visualized by ethidium bromide staining.

Temperature Gradient Gel Electrophoresis

Temperature gradient gel electrophoresis (TGGE) is based on the same underlying principles as denaturing gradient gel electrophoresis, except the denaturing gradient is produced by differences in temperature instead of differences in the concentration of a chemical denaturant. Standard TGGE utilizes an electrophoresis apparatus with a temperature gradient running along the electrophoresis path. As samples migrate through a gel with a uniform concentration of a chemical denaturant, they encounter increasing temperatures. An alternative method of TGGE, temporal temperature gradient gel electrophoresis (TTGE or tTGGE) uses a steadily increasing temperature of the entire electrophoresis gel to achieve the same result. As the samples migrate through the gel the temperature of the entire gel increases, leading the samples to encounter increasing temperature as they migrate through the gel. Preparation of samples, including PCR amplification with incorporation of a GC clamp, and visualization of products are the same as for denaturing gradient gel electrophoresis.

Single-Strand Conformation Polymorphism Analysis

Target sequences or alleles at the BPI locus can be differentiated using single-strand conformation polymorphism analysis, which identifies base differences by alteration in electrophoretic migration of single stranded PCR products, as described in Orita et al., Proc. Nat. Acad. Sci. 85:2766–2770 (1989). Amplified PCR products can be generated as described above, and heated or otherwise denatured, to form single stranded amplification products. Single-stranded nucleic acids may refold or form secondary structures which are partially dependent on the base sequence. Thus, electrophoretic mobility of single-stranded amplification products can detect base-sequence difference between alleles or target sequences.

Chemical or Enzymatic Cleavage of Mismatches

Differences between target sequences can also be detected by differential chemical cleavage of mismatched base pairs, as described in Grompe et al., Am. J. Hum. Genet. 48:212–222 (1991). In another method, differences between target sequences can be detected by enzymatic cleavage of mismatched base pairs, as described in Nelson et al., Nature Genetics 4:11–18 (1993). Briefly, genetic material from a patient and an affected family member may be used to generate mismatch free heterohybrid DNA duplexes. As used herein, "heterohybrid" means a DNA duplex strand comprising one strand of DNA from one person, usually the patient, and a second DNA strand from another person, usually an affected or unaffected family member. Positive selection for heterohybrids free of mismatches allows determination of small insertions, deletions or other polymorphisms that may be associated with alterations in androgen metabolism.

Non-PCR Based DNA Diagnostics

The identification of a DNA sequence linked to BPI can be made without an amplification step, based on polymorphisms including restriction fragment length polymorphisms in a patient and a family member. Hybridization probes are generally oligonucleotides which bind through complementary base pairing to all or part of a target nucleic acid. Probes typically bind target sequences lacking complete complementarity with the probe sequence depending on the stringency of the hybridization conditions. The probes are preferably labeled directly or indirectly, such that by assaying for the presence or absence of the probe, one can detect the presence or absence of the target sequence. Direct labeling methods include radioisotope labeling, such as with 32P or 35S. Indirect labeling methods include fluorescent tags, biotin complexes which may be bound to avidin or streptavidin, or peptide or protein tags. Visual detection methods include photoluminescents, Texas red, rhodamine and its derivatives, red leuco dye and e, e', 5, 5'-5354amethylbenzidine (TMB), fluorescein, and its derivatives, dansyl, umbelliferone and the like or with horse radish peroxidase, alkaline phosphatase and the like.

Hybridization probes include any nucleotide sequence capable of hybridizing to the porcine chromosome where BPI resides, and thus defining a genetic marker linked to BPI, including a restriction fragment length polymorphism, a hypervariable region, repetitive element, or a variable number tandem repeat. Hybridization probes can be any gene or a suitable analog. Further suitable hybridization probes include exon fragments or portions of cDNAs or genes known to map to the relevant region of the chromosome.

Preferred tandem repeat hybridization probes for use according to the present invention are those that recognize a small number of fragments at a specific locus at high stringency hybridization conditions, or that recognize a larger number of fragments at that locus when the stringency conditions are lowered.

One or more additional restriction enzymes and/or probes and/or primers can be used. Additional enzymes, constructed probes, and primers can be determined by routine experimentation by those of ordinary skill in the art and are intended to be within the scope of the invention.

Although the methods described herein may be in terms of the use of a single restriction enzyme and a single set of primers, the methods are not so limited. One or more additional restriction enzymes and/or probes and/or primers can be used, if desired. Additional enzymes, constructed probes and primers can be determined through routine experimentation, combined with the teachings provided and incorporated herein.

Genetic markers for genes are determined as follows. Male and female animals of the same breed or breed cross or derived from similar genetic lineages are mated. The offspring with the beneficial trait are determined. RFLP analysis of the parental DNA is conducted as discussed above in order to determine polymorphisms in the selected gene of each animal. The polymorphisms are associated with the traits.

When this analysis is conducted and the polymorphism is determined by RFLP or other analysis, amplification primers may be designed using analogous human or other closely related animal known sequences. The sequences of many of the genes have high homology. Primers may also be designed using known gene sequences as exemplified in Genbank or even designed from sequences obtained from linkage data from closely surrounding genes. According to the invention, sets of primers have been selected which identify regions in polymorphic genes. The polymorphic fragments have been shown to be alleles, and each was shown to be associated with beneficial traits, such as disease resistance, for various breeds. Often genotype associated with this trait alternates for different breeds. This outcome is similar to the situation disclosed in U.S. Pat. No. 5,374,523 entitled "Allelic variants of Bovine Somatotropin gene: Genetic marker for Superior Milk Production in Bovine" where the inventor found an allelic polymorphism in the somatotropin gene and one allelic form was beneficial for jersey cows and the alternate form was beneficial for Holstein cows.

The reagents suitable for applying the methods of the invention may be packaged into convenient kits. The kits provide the necessary materials, packaged into suitable containers. At a minimum, the kit contains a reagent that identifies a polymorphism in the selected gene that is associated with a trait. Preferably, the reagent is a PCR set (a set of primers, DNA polymerase and 4 nucleoside triphosphates) that hybridize with the gene or a fragment thereof. Preferably, the PCR set is included in the kit. Preferably, the kit further comprises additional means, such as reagents, for detecting or measuring the detectable entity or providing a control. Other reagents used for hybridization, prehybridization, DNA extraction, visualization etc. may also be included, if desired.

The methods and materials of the invention may also be used more generally to evaluate animal DNA, genetically type individual animals, and detect genetic differences in animals. In particular, a sample of genomic DNA may be evaluated by reference to one or more controls to determine if a polymorphism in the gene is present. Preferably, RFLP analysis is performed with respect to the gene, and the results are compared with a control. The control is the result of a RFLP analysis of the gene of a different animal where the polymorphism of the gene is known. Similarly, the genotype of an animal may be determined by obtaining a sample of its mRNA or genomic DNA, conducting RFLP analysis of the gene in the DNA, and comparing the results with a control. Again, the control is the result of RFLP analysis of the same gene of a different animal. The results genetically type the pig by specifying the polymorphism in its selected gene. Finally, genetic differences among animals can be detected by obtaining samples of the mRNA or genomic DNA from at least two animals, identifying the presence or absence of a polymorphism in the gene, and comparing the results.

These assays are useful for identifying the genetic markers relating to disease resistance, as discussed above, for identifying other polymorphisms in the gene that may be correlated with other characteristics, and for the general scientific analysis of genotypes and phenotypes.

The genetic markers, methods, and kits of the invention are also useful in a breeding program to improve disease resistance in a breed, line, or population of animals. Continuous selection and breeding of animals that are at least heterozygous and preferably homozygous for a polymorphism associated with a beneficial trait such as disease resistance would lead to a breed, line, or population having higher numbers of offspring in each litter of the females of this breed or line. Thus, the markers are selection tools.

The examples and methods herein disclose certain genes which have been identified to have a polymorphism which is associated either positively or negatively with a beneficial trait that will have an effect on disease resistance of that animal. The identification of the existence of a polymorphism within a gene is often made by a single base alternative that results in a restriction site in certain allelic forms. A certain allele, however, as demonstrated and discussed herein, may have a number of base changes associated with it that could be assayed for which are indicative of the same polymorphism. Further, other genetic markers or genes may be linked to the polymorphisms disclosed herein so that assays may involve identification of other genes or gene fragments, but which ultimately rely upon genetic characterization of animals for the same polymorphism. Any assay which sorts and identifies animals based upon the allelic differences disclosed herein are intended to be included within the scope of this invention.

One of skill in the art, once a polymorphism has been identified and a correlation to a particular trait established, will understand that there are many ways to genotype animals for this polymorphism. The design of such alternative tests merely represent optimization of parameters known to those of skill in the art and are intended to be within the scope of this invention as fully described herein.

The markers are associated with innate immunity traits which are non pathogen specific, so while bacteria is used for challenge it is expected that these traits will improve animal health against a wide variety of diseases or challenges such as stress, viral pathogen, etc.

EXAMPLES

Example 1

Cloning, Sequencing, Polymorphism Identification and Mapping of Porcine Bactericidal Permeability Increasing Protein (BPI) Gene Total RNA was isolated from the pig spleen and first-strand cDNA synthesis was performed. Partial porcine BPI cDNA was isolated by RT-PCR using the primers designed from the homology sequences of human and bovine BPI cDNA. Using sequence comparison of RT-PCR products from different lines, several single nucleotide polymorphisms (SNPs) were observed. To develop DNA-based PCR detection, two pig specific primer pairs were designed for the region of exon 4 and 5, and the region of exon 10 and exon 11 based on pig BPI cDNA sequence. Then two sets of PCR-RFLPs (exon 4 and intron, and exon 10 and intron) markers were developed to perform population studies and conduct association analyses between BPI variation and pig disease resistance phenotypes. An about 300 base pair insertion/deletion polymorphism was also observed in intron 10. Using pig specific primers and PCR-RFLP markers, BPI was physically and linkage mapped to the pig chromosome 17.

Biology of BPI

Bactericidal/permeability-increasing protein (BPI) is a neutrophil granular pattern recognition molecule which has bactericidal activity on gram-negative bacteria (Elsbach and Weiss, 1998; Hoffmann et al., 1999). The cDNA sequence of BPI has been elucidated in several species, including human (Gray et al., 1989) and bovine (Leong et al., 1990) (but not pig), and the structure of human BPI gene has been analyzed (Hubacek et al., 1997). The crystal structure of human BPI showed that BPI consists of two functionally distinct domains: a potently antibacterial and anti-endotoxin amino-terminal domain and a carboxy-terminal portion that imparts opsonic activity to BPI (Elsbach et al., 1998).

Neutrophils in human newborns are deficient in BPI and the deficiency correlates with decreased antibacterial activity of newborn neutrophils (Levy et al., 1999). Levy et al. (2000) has developed a recombinant BPI peptide (rBPI23) to be tested as a drug to increase newborn innate immunology. This rBPI23, which consists of the Nh2-terminal portion of BPI, has been shown by in vivo studies (Nell et al (2000); see also papers discussed in review by Elsbach and Weiss, 1998) and ex vivo studies (Levy et al 2000) to contain anti-bacterial properties primarily through binding of the lipid A portion of lipopolysaccharide (LPS). On the other hand, the C-terminal portion has been shown to increase BPI protein stability (Bulow et al., 2000) as well as the opsonization of bacteria by neutrophils or monocytes in an in vitro model (Iovine et al, 1997).

A 23 kDa NH2-terminal fragment of human BPI (rBPI23) has been administered to LPS-treated pigs (Vandermeer et al., 1994). rBPI23 treatment had no effect on some immune responses (including serum TNF-alpha or thromboxane A2 levels), but did improve several negative effects in the lung associated with exposure to LPS such as alveolitis, hypoxemia, and pulmonary edema. Also, the increased expression of opsonin receptors on circulating phagocytes in response to LPS was decreased by rBPI23 administration (Vandermeer et al., 1994).

On the other hand, macrophage expressing BPI-IgG fusion protein were resistant to endotoxin (LPS) treatment and showed a decrease in the secretion of TNF-alpha (Dahlberg et al., 1996); a dampening effect on TNF-alpha production in response to LPS was also observed with human monocytes and in other systems (reviewed in Elsbach and Weiss, 1998). Thus the lack of an effect on TNF-alpha induction in pigs is contrary to BPI effects in other species, and may reflect either differences in species or in experimental conditions. Human BPI is believed to have activity against several gram-negative bacteria, and several bacterial species have been directly tested and shown to be susceptible to BPI protein; including several *Salmonella* species such as *Salmonella minnesota* (Ooi et al., 1991) and *Salmonella typhimurium* (Qi et al., 1995).

BPI Genetics

There have been two reports of genetic variability at the human BPI locus. Hollings and Gray (1994) reported the presence of a restriction fragment length polymorphism at human BPI, which was detected by Southern hybridization. This polymorphism was not localized within human BPI. Another polymorphism, detected by PstI digestion of a large PCR product, was also reported for human BPI (Hubacek et al. 1997). This polymorphism was mapped to intron 5, although specific sequence differences were not reported at this polymorphism. Using physical mapping techniques, BPI gene was assigned to human chromosome 20 (Gray et al., 1993).

Two batches of animals were experimentally challenged with salmonella, and infection related measurements were taken for 7 days post infection. Novel tests for polymorphisms at BPI were used to genotype the challenged animals. Association analysis revealed statistical association of BPI genotype with innate immune traits such as fecal bacteria counts, as well as several measures of immune cell numbers, during the challenge. Controlling fecal bacterial counts has economic value as an infected animal is the main source of transmission to healthy animals. Thus a marker that would identify animals with decreased fecal bacterial counts would be valuable and have utility.

Genetic Information and Marker Technology for variability at the BPI Gene

Set I (BPI-AvaII)

```
Primer sequences
Forward: GGT GGC AAC TTT GAC CTG AG    (SEQ ID NO:1)

Reverse: CAT CGG AGG TCT CTG GAC AAG  (SEQ ID NO:2)
```

Amplification annotations. This primer pair amplifies a 540 bp product containing 153 bp exon 4 and 387 bp intron 4 of the porcine BPI gene.

PCR Conditions

Mg++conc 1.5 mM, dNTPs-conc 200.0 µM, Taq 0.375U
Cycle profile 95 C for 3 min; 40×[94c for 45s; 55 C for 45s; 72 C for 1 min] 72 C for 5 min.

PCR-Annotation. Amplification was performed using 25 ng of genomic DNA and 0.5 µM of each primer in a reaction volume of 10 µl.

PCR-RFLP markers
Alleles detected by PCR-RFLP markers

| Enzyme | Allele | Recognition site | base | Size of Fragments (base pairs) |
|---|---|---|---|---|
| AvaII | 1 | 103 | G | 417, 123 |
|  | 2 | 103 | A | 540 |

Polymorphism at position 103 is detected by AvaII digestion and by using 2.5% agarose gel.

Chromosome location. BPI was physically located on pig chromosome 17(½) q21–q23 by using pig/rodent somatic cell hybrid panel (SCHP) comprising 27 cell lines. Linkage mapping from AvaII genotyping of PiGMaP reference families showed that the most possible gene order with BPI on pig chromosome 17 was S0204-8.6-S0359-3.1-SW1031-15.4-BPI-10.3-SW840.

Allele frequencies. Allele C3 (AvaII digestion) was observed with a frequency of 100% in Yorkshire (n=9), Hampshire (n=6), Duroc (n=8), Landrace (n=8), Large white (n=11) and wild boar n=2). Allele C3 was detected with a frequency of 31.25% in Meishan (n=16) and 93.75% in a partially related commercial population. The sequence amplified is shown in FIG. 1 (SEQ ID NO:3) sequence does not include primer sequences)

Note: a) Bold text are exon 4 sequences and regular text are intron sequences.
b) R=A or G.

Set II (BPI-HpaII)

```
Primer sequence
Forward   CCC AAC ATG GAG ATG CAG TTC  (SEQ ID NO:4)
primer:

Reverse   CAA TGA ATC AAT GAG CAC ACC  (SEQ ID NO:5)
primer:
```

Amplification annotation. This primer pair amplifies a 445 bp product containing 153 bp exon 10 and 292 bp intron 10 of the porcine BPI gene.

PCR Conditions

Mg++conc 1.5 mM, dNTPs-conc 200.0 µM, Taq 0.375U
Cycle profile 95 C for 3 min; 40×[94c for 45s; 60 C for 45s; 72 C for 45s], 72 C for 5 min.

PCR-Annotation. Amplification was performed using 25 ng of genomic DNA and .5 µM of each primer in a reaction volume of 10 µl.

Alleles detected by PCR-RFLP markers

| Enzyme | Allele | Recognition site | base | fragments |
|---|---|---|---|---|
| HpaII | 3 | 122 | T | 445 |
|  | 4 | 122 | G | 304, 142 |

Polymorphism at position 122 is detected by HpaII digestion and by using 2.5% agarose gel.

Allele frequencies Allele 3 (HpaII digestion) was observed with a frequency of 93.67% in a partially related commercial population (n=79). The amplified sequence is shown in FIG. 2 SEQ ID NO: 6, Sequence (not including primer sequences).

Note: a) Bold text are exon 10 sequences and regular text are intron sequences.
b) K=G or T.

Set III (BPI-Length polymorphism)

```
Primer sequence
Forward: CCC AAC ATG GAG ATG CAG TTC  (SEQ ID NO:4)

Reverse: AAG CCT TTT GGA CCG GAC AC    (SEQ ID No:7)
```

Amplification annotations. This primer pair amplifies a 1309 bp product containing 153 bp exon 10, 1110 bp intron 10 and 46 bp intron 11 of the porcine BPI gene.

PCR Conditions

Mg++conc 1.5 mM, dNTPs-conc 200.0 µM, Taq 0.375U
Cycle profile 95 C for 3 min; 40×[94 C for 1 min; 60 C for 1 min; 72 C for 1.5 min] 72 C for 5 min.

PCR-Annotation. Amplification was performed using 25 ng of genomic DNA and 0.5µM of each primer in a reaction volume of 10 µl.

Length polymorphism. A length polymorphism was observed between 1309 bp fragment (Allele 5) and about 1600 bp fragment (Allele 6).

Allele frequencies allele 5 was observed with a frequency of 13.86% in a partially related commercial population (n=83).

Sequences (not including primer sequences) is shown in FIG. 3 SEQ ID NO:8.

Note: a) Bold text are exon 10 and exon 11 sequences and regular text are intron sequences.
b) ☐ represent about 300 bp insertion present in allele 6. This inserted sequence is a repetitive region that is difficult to sequence accurately.

Additional novel porcine BPI sequence information: Full length coding region sequence of porcine BPI and alignment of full-length sequence of each allele (3,4) at the DNA level and the protein level. This cDNA sequence was obtained by using novel primers to amplify BPI cDNA fragments from mRNA converted to cDNA. Partially overlapping cDNA fragments were then sequenced to determine the complete sequence. The result is depicted in FIGS. 4a (nucleotide) and 4b (amino acid).

Example 1

Bacterial Challenge and Association Testing

Summary

To test the marker assays to identify animals differing for innate immunity traits, two batches of animals were experimentally challenged with *Salmonella cholerasuis* and infection related measurements were taken post infection. Three different polymorphism tests at the BPI gene (BPI Ava II, BPI Hpa II, BPI-LP) were used to classify challenged animals, and all three assigned animals to classes which showed significant differences for innate immunity as shown by fecal shedding of bacteria at the end of the challenge (FMPND6). In many cases, additional traits related to the immune system such as: the number of neutrophils, monocytes or white blood cells at the end of the challenge; the difference in these cell numbers, as well as lymphocytes, at the beginning of the challenge versus the end were also statistically associated with specific BPI genotypes. The percentage of neutrophils or lymphocytes at either the beginning or end of the challenge was also associated with BPI genotypes.

Importantly, the BPI HpaII genetic test identifies animals with different BPI proteins because the sequence of the individual Hpa II alleles show different protein sequences are encoded by the different BPI HpaII alleles. The BPI protein is important in the early response to gram-negative bacterial infection, thus an association of BPI genotypes with fecal shedding at the end of the challenge is consistent with an altered function of BPI in these classes of animals.

Controlling fecal bacterial counts has economic value as an infected animal is the main source of transmission of the disease to healthy animals. Thus a marker that would identify animals with decreased fecal bacterial counts would be valuable and have utility.

Protocol

Pregnant sows were pre-selected based on data from preliminary BPI1 genotype analysis and a crude in vitro macrophage bactericidal assay results. From these sows, two separate experiments of 42 piglets (8–19 days old) were derived and piglets shipped to isolation facilities. Piglets consisted of 2 lines of pigs from two different farms. Piglets were determined to be *Salmonella*-free by frequent bacterial culture of fecal material. Piglets were divided into principals and controls and grown to 7–9 weeks of age prior to intranasal challenge with 1 billion colony forming units of *Salmonella choleraesuis* χ3246. The control group (saline inoculated) consisted of 1 piglet/litter (Exp #1, n=13; Exp #2, n=12). The principal group (*Salmonella* infected) consisted of 2 or 3 piglets/litter (Exp #1, n=29; Exp #2, n=30). Following challenge, animals were monitored daily for temperature, clinical signs and *Salmonella* shedding (qualitative and quantitative). Pigs were necropsied post *S. choleraesuis* or saline inoculation and quantitative bacteriology (most probable number) was performed on ileocecal lymph node and from fecal samples at the end of the challenge. Blood samples were drawn at specific intervals during challenge and standard complete blood count (CBC) were performed. Portions of mesenteric lymph node, spleen, liver, lung, and muscle were collected and frozen in liquid nitrogen for DNA analysis. Results are shown in Tables Ex1-1 to Ex1-3, and genotype frequencies within this challenge population for each of the markers is shown in Table Ex1-4.

Statistical Treatment of Data

Phenotypic and genotype data were available on 59 challenged animals from lines A and B (15 and 44 respectively). See Table Ex1-4 for genotype frequencies. Three markers in BPI were genotyped.

Least square means were estimated for the 3 genotype classes from the following model:

Trait=sow id+experiment+barn+genotype with sowid as random effect and experiment and barn as fixed effects. Significance p-values for genotype were also recorded from this model.

Results and Discussion

Overall results are summarized in Tables Ex1-1-3. The data were log transformed for the following traits: all bacterial counts, as well as macro1, macro2, mono2 and wbc1, because of the non-normal distribution of the data. Log transformation is a widely accepted treatment for non-normally distributed data sets.

Statistical association is defined as a comparison between phenotype and genotype that show a P value less that 0.1; i.e., a statistical term that indicates the declared statistically significant difference between classes being compared has a confidence of greater than 90% of being correct. Several associations have even higher levels of confidence, such as P values less than 0.05 or even less than 0.01 (see individual Results in Tables below).

As can be seen from the data, BPI genotypes determined by all BPI marker systems were associated with differences in fecal bacterial counts (FMPND6; fecal bacterial count on day 6 of challenge). The data also shows that BPI genotypes, determined by one or more BPI markers, are associated with several innate immune defense parameters. These parameters are critical for control of and recovery from infection, and include fever (temperature) and numbers of immune cells before and after infection. Some alleles are found to be associated with traits in only one of the analyses, often due to lack of informativeness of the marker.

TABLE Ex1-1

BPI AvaII genotype association analysis in example 1.

| | Line A | | | |
|---|---|---|---|---|
| | LS Means (s.e.)** | | | |
| Trait* | 11 | 12 | 22 | P value |
| tempD7 | 40.4 (.18) c | 41.1 (.29) d | — | 0.08 |
| FMPND6 | .44 (1.1) g | 1.84 (1.1) h | — | 0.006 |
| neut1 | 8.76 (.70) | 8.00 (.91) | — | .42 |
| neut2 | 7.56 (2.6) e | 2.68 (2.8) f | — | .02 |
| neut_diff | −1.17 (2.8) g | −5.35 (2.9) h | — | .008 |
| mono1 | 1.17 (.29) | 1.42 (.36) | — | .45 |
| mono2 | .37 (.13) c | .09 (.15) d | — | .05 |
| mono_diff | 1.51 (.80) e | −.34 (.89) f | — | .02 |
| wbc1 | 1.31 (.04) | 1.25 (.05) | — | .31 |
| wbc2 | 22.7 (2.9) c | 16.5 (3.4) d | — | .06 |
| wbc_diff | 2.10 (3.5) a | −2.3 (4.1) b | — | .21 |

*Traits are: TEMPDO = temperature on day 0 of challenge, TEMPD1- temperature on day 1 after challenge, etc; ICLND7 = Salmonella count in ileocecal lymph node on day 7 post challenge; FMPND6 = mean fecal Salmonella count on day 6 after challenge; Macro 1 and 2 = macrophage numbers before (1) and after (2) challenge; Macro_diff = difference in macrophage numbers before and after challenge; lymph 1, 2, diff = lymphocyte numbers before (1) and after (2)challenge and the difference between these values; pneut1,2, diff = percentage of neutrophils before (1) and after (2) challenge and the difference between these values; plymph 1, 2, diff = percentage of lymphocytes before (1) and after (2) challenge and the difference between these values.

**Significant differences (p values) for LS means are indicated as follows:

a–b p <.30 c–d p <.10 e–f p <.05 g–h p <.01 i–j p <.005 k–l p <.001

TABLE Ex 1-2

BPI HpaII genotype association analysis in example 1.

| | Line A | | | | Line B | | | |
|---|---|---|---|---|---|---|---|---|
| | LS means (s.e.)** | | | P | LS means (s.e.)** | | | P |
| Trait* | 33 | 34 | 44 | value | 33 | 34 | 44 | value |
| tempD0 | 39.7 (.16) | 39.9 (.19) | — | 0.52 | 39.6 (.06) | 39.4 (.26) | — | 0.52 |
| tempD1 | 39.7 (.10) | 39.8 (.12) | — | 0.38 | 39.6 (.06) e | 38.9 (.28) f | — | 0.02 |
| tempD2 | 41.4 (.6) | 41.5 (.22) | — | 0.67 | 41.3 (.11) | 41.1 (.50) | — | 0.71 |
| FMPND6 | .18 (.87) g | 1.57 (.87) h | — | 0.006 | −.27 (.22) e | 2.16 (.91) f | — | 0.03 |
| neut1 | 9.03 (.78) | 8.70 (.90) | — | .71 | 7.15 (.39) a | 4.15 (1.8) b | — | .12 |
| neut2 | 8.77 (2.7) e | 4.16 (2.8) f | — | .02 | 8.80 (.51) a | 11.8 (2.38) b | — | .23 |
| neut_diff | −.37 ((2.6) g | −4.45 (2.6) h | — | .009 | 1.65 (.54) e | 7.67 (2.5) f | — | .03 |
| lymph1 | 10.1 (1.2) | 9.01 (1.5) | — | .50 | 8.72 (.72) | 11.1 (3.04) | — | .46 |
| lymph2 | 7.73 (.82) | 7.87 (1.2) | — | .93 | 9.42 (.50) a | 6.83 (2.3) b | — | .28 |
| lymph_diff | −2.23 (1.6) | −1.41 (1.9) | — | .71 | .67 (.67) c | −4.53 (2.8) d | — | .09 |
| mono1 | 1.15 (.26) | 1.37 (.30) | — | .48 | 1.03 (.09) | .70 (.40) | — | .44 |
| mono2 | .39 (.12) c | .13 (.13) d | — | .06 | .18 (.04) e | .58 (.16) f | — | .02 |
| mono_diff | 1.62 (.72) e | −.14 (.77) f | — | .02 | .67 (.15) i | 3.22 (.68) j | — | .002 |
| pneut1 | 42.7 (3.0) | 46.0 (3.6) | — | .39 | 43.6 (2.5) c | 23.4 (10.6) d | — | .08 |
| pneut2 | 32.2 (10) | 57.4 (19) | — | .37 | — | — | — | — |
| pneut_diff | −10.7 (13) | 5.62 (25) | — | .62 | — | — | — | — |
| plymph1 | 48.5 (3.3) | 44.7 (3.8) | — | .34 | 48.4 (2.5) c | 70.0 (11) d | — | .06 |
| plymph2 | 37.5 (2.7) | 30.8 (7.0) | — | .47 | — | — | — | — |
| plymph_d | −11.0 (4.5) | −10.6 (11) | — | .98 | — | — | — | — |
| wbc1 | 1.31 (.04) | 1.28 (.04) | — | .47 | 1.23 (.02) | 1.19 (.07) | — | .58 |
| wbc2 | 23.9 (3.1) c | 18.3 (3.3) d | — | .08 | 22.0 (.64) a | 26.7 (3.0) b | — | .14 |
| wbc_diff | 2.65 (3.2) | −1.11 (3.6) | — | .26 | 4.63 (.71) c | 10.8 (3.3) d | — | .08 |

*Traits are: TEMPD0 = temperature on day 0 of challenge, TEMPD1—temperature on day 1 after challenge, etc.;
ICLND7 = Salmonella count in ileocecal lymph node on day 7 post challenge; FMPND6 = mean fecal Salmonella count on day 6 after challenge; Macro 1 and 2 = macrophage numbers before (1) and after (2) challenge;
Macro_diff = difference in macrophage numbers before and after challenge; lymph 1, 2, diff = lymphocyte numbers before (1) and after (2) challenge and the difference between these values; pneut1, 2, diff = percentage of neutrophils before (1) and after (2) challenge and the difference between these values; plymph 1, 2, diff = percentage of lymphocytes before (1) and after (2) challenge and the difference between these values.
**Significant differences (p values) for LS means are indicated as follows: a-b, p < .30; c-d, p < .10; e-f, p < .05; g-h, p < .01; i-j, p < .005; k-l, p < .001

TABLE Ex 1-3

BPI length polymorphism genotype association analysis in example 1.

| | Line A | | | | Line B | | | |
|---|---|---|---|---|---|---|---|---|
| | LS means (s.e.)** | | | P | LS means (s.e.)** | | | P |
| Trait* | 55 | 56 | 66 | value | 55 | 56 | 66 | value |
| FMPND6 | — | 1.33 (.99) g | −.04 (1.0) h | 0.006 | — | −.01 (.50) | −.12 (.29) | 0.84 |
| lymph1 | — | 9.50 (1.4) | 10.2 (1.3) | .65 | — | 10.2 (1.3) a | 8.30 (.76) b | .18 |
| lymph2 | — | 7.72 (1.0) | 8.14 (.88) | .77 | — | 9.08 (1.0) | 9.47 (.56) | .74 |
| lymph_diff | — | −1.92 (1.9) | −1.77 (1.7) | .94 | — | −1.19 (1.2) c | 1.18 (.73) d | .10 |
| plymph1 | — | 46.5 (3.7) | 48.7 (3.5) | .48 | — | 52.1 (4.7) | 47.8 (2.8) | .44 |
| plymph2 | — | 28.3 (4.2) c | 41.8 (4.1) d | .09 | — | 51.6 (5.3) | 45.3 (3.2) | .34 |
| plymph_d | — | −17.4 (8.2) | −8.9 (7.4) | .49 | — | −7.69 (6.4) | −7.19 (4.0) | .95 |
| wbc1 | — | 1.29 (.04) | 1.31 (.04) | .65 | — | 1.27 (.03) a | 1.21 (.02) b | .10 |
| wbc2 | — | 20.4 (3.0) c | 24.2 (2.9) d | .09 | — | 22.2 (1.3) | 22.4 (.74) | .91 |
| wbc_diff | — | −.03 (3.4) a | 3.26 (3.2) b | .20 | — | 3.01 (1.4) a | 5.67 (.80) b | .12 |

*Traits are: TEMPD0 = temperature on day 0 of challenge, TEMPD1—temperature on day 1 after challenge, etc.;
ICLND7 = Salmonella count in ileocecal lymph node on day 7 post challenge; FMPND6 = mean fecal Salmonella count on day 6 after challenge; Macro 1 and 2 = macrophage numbers before (1) and after (2) challenge;
Macro_diff = difference in macrophage numbers before and after challenge; lymph 1, 2, diff = lymphocyte numbers before (1) and after (2) challenge and the difference between these values; pneut1, 2, diff = percentage of neutrophils before (1) and after (2) challenge and the difference between these values; plymph 1, 2, diff = percentage of lymphocytes before (1) and after (2) challenge and the difference between these values.
**Significant differences (p values) for LS means are indicated as follows: a-b, p < .30; c-d, p < .10; e-f, p < .05; g-h, p < .01; i-j, p < .005; k-l, p < .001

TABLE Ex1-4

BPI Genotype frequencies for example 1.

| | Line | 11 | 12 | 22 |
|---|---|---|---|---|
| BPIavaII | A | 10 | 4 | — |
| | B | 44 | — | — |
| | | 33 | 34 | 44 |
| BpIhpaI | A | 10 | 5 | — |
| | B | 39 | 2 | — |
| | | 55 | 56 | 66 |
| BPI_Ip | A | — | 6 | 8 |
| | B | — | 10 | 32 |

Example 2

Bacterial Challenge and Association testing

Summary

To further assess the utility of the marker tests to identify animals that differ in innate disease resistance, some BPI markers were tested on offspring of sires that were susceptible or resistant to Salmonellosis. The offspring were challenged orally with *S. choleraesuis* and infection and innate immunity related traits were measured. Association analyses revealed that potential effects of BPI genotype on bacterial load in liver and immune cell numbers and function. The presence of bacteria in internal organs demonstrates that the animal's immune system was unable to control spread of the infection. Reduced bacterial counts and lower fever in one genotype class are indicative of the heightened ability of those animals to control infection. These traits have economic value since fever and systemic infection decrease appetite and suppress growth and performance in a measurable way.

Experiment Description

Challenged pigs were produced as part of a reference population that was bred from sires was that differed in susceptibility to salmonellosis. The founder sires were selected based on the results of a preliminary study to identify individuals that differed in susceptibility to infection with *S. choleraesuis*. Sires (commercial line Y) were mated to 23 F1 gilts (crosses of commercial lines Y×Z and Z×Y) and produced one litter. Three to nine piglets from each litter were selected for oral challenge with $8 \times 10^8$ *S. choleraesuis* (n=216). Piglets were challenged at 6 weeks of age. Clinical signs and fever were monitored during the one week infection period. Blood samples were taken from animals for innate immunity studies one week before challenge, on the day of challenge and at necropsy. Traits of innate immunity included total leukocyte count and differential, bacterial uptake, phagocytosis and killing by neutrophils, and lymphocyte proliferation against several antigens. One week after challenge, animals were necropsied and the amount of Salmonella in liver and spleen was determined by quantitative culture on one gram of tissue. DNA was also isolated from blood for genetic analysis. Pigs were genotyped by using BPI marker systems described above; genotype frequencies are shown in Table Ex2-1. Statistical associations between genotypes and measured traits are shown in Tables Ex2-2, Ex2-3.

Statistical Treatment of Data

The associations between the sequence polymorphisms and phenotypes were tested using mixed model procedures (SAS™ procedure MIXED) with a model which always included dam as a random effect and marker parameters and Group as fixed effects. Single point significance values are reported, without making adjustments for multiple comparisons.

Least square means were estimated for the 3 genotype classes from the following model, with sowid as random effect and experiment and barn as fixed effects:

Trait=sowid+experiment+barn+genotype.

Results and Discussion

Overall results are summarized in Tables Ex2-2, Ex2-3. The bacterial count data (LiverC) was log transformed because of the non-normal distribution of the data, a widely accepted treatment for non-normally distributed data sets. As can be seen from the data in Example 2, BPI genotypes are associated with differences in bacterial levels in the liver, with numbers of lymphocytes and neutrophils, with lymphocyte function (as measured by stimulation index) and with uptake of bacteria by neutrophils (see Tables Ex2-2, Ex2-3). Some alleles are found to be associated with traits in only one of the analyses, often due to lack of informativeness of the marker.

TABLE Ex2-1

Genotype frequencies within example 2 population.

| genotype | | 11 | 12 | 22 | total |
|---|---|---|---|---|---|
| BPI-HpaII | number | 127 | 41 | 6 | 174* |
| | percentage | 73 | 24 | 3 | 100 |
| BPI-LP | number | 4 | 44 | 122 | 170* |
| | percentage | 2 | 26 | 72 | 100 |

*not all animals genotyped for BPI-LP marker

TABLE Ex2-2

BPI HpaII genotypes association analysis in example 2

| BPI HpaII | LSmeans (s.e.) | | |
|---|---|---|---|
| Trait | 11 | 12 | 22 |
| liverC | 2.24 (0.15) c | 2.18 (0.23) c | 3.33 (0.63) d |
| lym1 | 56.43 (1.01) a | 59.12 (1.78) b | 56.29 (5.12) |
| lym2 | 59.76 (0.96) c | 58.69 (1.60) a | 51.99 (4.50) d b |
| lym3 | 46.59 (1.08) | 46.46 (1.88) | . ( . ) |
| neu1 | 39.56 (1.05) a | 36.81 (1.76) b | 39.67 (4.95) |
| neu2 | 36.62 (0.90) a | 37.34 (1.56) a | 44.00 (4.47) b |
| neu3 | 49.10 (1.15) | 48.66 (1.92) | . ( . ) |
| SICA_pre | 210.1 (25.8) o | 221.4 (43.6) o | 891.8 ( 123) p |
| SICA_pos | 62.22 (12.2) | 86.52 (23.5) | . ( . ) |
| uptake | 0.34 (0.14) e | 0.91 (0.24) f | 0.68 (0.68) |

| LSmeans significance levels: | |
|---|---|
| a–b | p < .3 |
| c–d | p < .1 |
| e–f | p < .05 |
| g–h | p < .01 |
| i–j | p < .005 |
| k–l | p < .001 |
| m–n | p < .0005 |
| o–p | p < .0001 |

TABLE Ex2-2-continued

BPI HpaII genotypes association analysis in example 2

Description of traits

| Trait | Description |
| --- | --- |
| liverC | Bacterial counts in liver at one week |
| lym1 | percentage lymphocytes on day 15 |
| lym2 | percentage lymphocytes on day 29 |
| lym3 | percentage lymphocytes on day 38 or post mortem |
| neu1 | percentage neutrophils on day 15 |
| neu2 | percentage neutrophils on day 29 |
| neu3 | percentage neutrophils on day 38 or post mortem |
| SICA_pos | Stimulation index in presence of Concavalin A on day 38 |
| SICA_pre | Stimulation index in presence of Concavalin A on day 29 |
| uptake | Salmonella uptake efficiency of PMN's |

TABLE ex2-3

BPI LP genotypes association analysis in example 2

| BPI length pI | LSmeans (s.e.) | | |
| --- | --- | --- | --- |
| Trait | 11 | 12 | 22 |
| liverC | 1.96 (0.64) | 2.22 (0.23) | 2.29 (0.15) |
| lym1 | 53.67 (5.19) a | 60.03 (1.79) b C | 56.17 (1.04) d |
| lym2 | 57.75 (4.66) | 59.33 (1.65) | 59.20 (1.00) |
| lym3 | 35.10 (5.85) e c | 48.74 (1.95) f | 46.94 (1.12) d |
| neu1 | 41.27 (5.05) | 35.81 (1.78) c | 39.89 (1.07) d |
| neu2 | 38.65 (4.63) | 36.69 (1.61) | 37.15 (0.95) |
| neu3 | 59.81 (5.86) e c | 46.74 (1.99) f | 48.67 (1.18) d |
| SICA_pre | 242.6 (135) | 257.4 (47.1) | 217.0 (27.8) |
| SICA_pos | 66.44 (76.4) | 90.49 (25.1) | 61.46 (13.0) |
| uptake | 0.50 (0.70) | 0.94 (0.25) e | 0.33 (0.14) f |

LSmeans significance levels:

| | |
| --- | --- |
| a–b | $p < .3$ |
| c–d | $p < .1$ |
| e–f | $p < .05$ |
| g–h | $p < .01$ |
| i–j | $p < .005$ |
| k–l | $p < .001$ |
| m–n | $p < .0005$ |
| o–p | $p < .0001$ |

Description of traits

| Trait | Description |
| --- | --- |
| liverC | Bacterial counts in liver at one week |
| lym1 | percentage lymphocytes on day 15 |
| lym2 | percentage lymphocytes on day 29 |
| lym3 | percentage lymphocytes on day 38 or post mortem |
| neu1 | percentage neutrophils on day 15 |
| neu2 | percentage neutrophils on day 29 |
| neu3 | percentage neutrophils on day 38 or post mortem |
| SICA_pos | Stimulation index in presence of Concavalin A on day 38 |
| SICA_pre | Stimulation index in presence of Concavalin A on day 29 |
| uptake | Salmonella uptake efficiency of PMN's |

REFERENCES

Elsbach P, Weiss J 1998 Role of the bactericidal/permeability-increasing protein in host defense. Curr Opin Immunol 10:45–9

Gray P W, Flaggs G, Leong S R, Gumina R J, Weiss J, Ooi C E, Elsbach P 1989 Cloning of the cDNA of a human neutrophil bactericidal protein. Structural and functional correlations. J Biol Chem 264:9505–9.

Gray P W, Corcorran A E, Eddy R L Jr, Byers M G, Shows T B 1993 The genes for the lipopolysaccharide binding protein (LBP) and the bactericidal permeability increasing protein (BPI) are encoded in the same region of human chromosome 20. Genomics 15:188–90.

Hoffmann J A, Kafatos F C, Janeway C A, Ezekowitz R A 1999 Phylogenetic perspectives in innate immunity. Science 1999 284:1313–8.

Hubacek J A, Buchler C, Aslanidis C, Schmitz G 1997 The genomic organization of the genes for human lipopolysaccharide binding protein (LBP) and bactericidal permeability increasing protein (BPI) is highly conserved. Biochem Biophys Res 236:427–30.

Leong S R, Camerato T 1990 Nucleotide sequence of the bovine bactericidal permeability increasing protein (BPI). Nucleic Acids Res 18:3052.

Levy O, Martin S, Eichenwald E, Ganz T, Valore E, Carroll S F, Lee K, Goldmann D, Thorne G M 1999 Impaired innate immunity in the newborn: newborn neutrophils are deficient in bactericidal/permeability-increasing protein. Pediatrics 104(6):1327–33.

Levy O, Sisson R B, Kenyon J, Eichenwald E, Macone A B, Goldmann D 2000 Enhancement of neonatal innate defense:

effects of adding an N-terminal recombinant fragment of bactericidal/permeability-increasing protein on growth and tumor necrosis factor-inducing activity of gram-negative bacteria tested in neonatal cord blood ex vivo. Infect Immun 68(9):5120–5.

OVERALL SUMMARY

In both Examples, BPI genotypes are associated with specific measures of innate disease resistance and disease susceptibility such as systemic infection and immune cell numbers and/or function. Thus this information and marker systems to determine BPI genotypes can be used to improve animal health and performance due to the ability to decrease incidence of disease through identifying susceptible animals before they can become sick. Alternatively, the same technologies described above can be used to identify those animals most likely to be the healthiest within a group. Improving these traits have economic value since fever and systemic infection decrease appetite and suppress growth and perfomance.

What is claimed is:

1. A method of screening pigs to determine those with different disease resistance or innate immunity traits comprising:
   obtaining a sample of genetic material from said pig;
   assaying for the presence of a nucleotide present at position 103 of exon 4 in the BPI gene of said pig and determining disease resistance or innate immunity traits in said pig, wherein the presence of a G at nucleotide position 103 indicates that said pig has an increased likelihood of having one or more of the following disease resistance and/or immunity traits after challenge with *Salmonella cholerasuis*:
   decreased temperature 7 days after challenge,
   decreased fecal bacterial count 6 days after challenge,
   decreased change in the number of neutrophils,
   increased number of monocytes after challenge, or
   increased white blood cell count,
   when compared to a pig with an A at position 103.

2. The method of claim 1 wherein the presence of a G at nucleotide position 103 is identifiable by an Ava II, restriction enzyme or a length polymorphism.

3. A method of screening pigs to determine those with different disease resistance or innate immunity traits comprising:
   obtaining a sample of genetic material from said pig;
   assaying for the presence of a nucleotide present at position 122 of exon 10 in the BPI gene of said pig and determining disease resistance or innate immunity traits in said pig wherein the presence of a G at nucleotide position 122 indicates that said pig has an increased likelihood of having one or more of the following disease resistance and/or immunity traits after challenge with *Salmonella cholerasuis*:
   decreased fecal *Salmonella cholerasuis* count 6 days after challenge, or
   lower difference in the number of neutrophils,
   when compared to a pig with a T at nucleotide position 122.

4. The method of claim 3 wherein the presence of a G at nucleotide position 122 is identifiable by an Hpa II, restriction enzyme or a length polymorphism.

* * * * *

UNITED STATES PATENT AND TRADEMARK OFFICE
CERTIFICATE OF CORRECTION

| | | |
|---|---|---|
| PATENT NO. | : 7,070,929 B2 | Page 1 of 1 |
| APPLICATION NO. | : 10/161968 | |
| DATED | : July 4, 2006 | |
| INVENTOR(S) | : Tuggle, Christopher K. et al. | |

It is certified that error appears in the above-identified patent and that said Letters Patent is hereby corrected as shown below:

Front Cover Page Under (73):
Assignees: Iowa State University Research Foundation, Inc., Ames, IA (US); Pig "Inprovement" --Improvement-- Company UK Limited (GB); The United States of America as represented by the Secretary of Agriculture, Washington, DC (US)

Signed and Sealed this

Fifteenth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 7,070,929 B2
APPLICATION NO. : 10/161968
DATED : July 4, 2006
INVENTOR(S) : Tuggle, Christopher K. et al.

It is certified that error appears in the above-identified patent and that said Letters Patent is hereby corrected as shown below:

Column 1, lines 10-14:
DELETE:
"GRANT REFERENCE
Work for this invention was funded in part by ISU Grant
No. 400-43-71-21-3337. The Government may have certain rights in this invention."

Signed and Sealed this

Fifth Day of September, 2006

JON W. DUDAS
*Director of the United States Patent and Trademark Office*